(12) United States Patent
Karpf

(10) Patent No.: US 6,334,192 B1
(45) Date of Patent: Dec. 25, 2001

(54) COMPUTER SYSTEM AND METHOD FOR A SELF ADMINISTERED RISK ASSESSMENT

(76) Inventor: Ronald S. Karpf, 11425 Brandy Hall La., Gaithersburg, MD (US) 20878

( * ) Notice: Subject to any disclaimer, the term of this patent is extended or adjusted under 35 U.S.C. 154(b) by 0 days.

(21) Appl. No.: 09/037,165

(22) Filed: Mar. 9, 1998

(51) Int. Cl.[7] .................................................. G06F 11/00
(52) U.S. Cl. ............................ 714/1; 600/300; 128/924; 128/920; 705/2
(58) Field of Search ................................... 700/90; 705/2; 707/104; 706/45, 924; 600/300; 128/920, 924; 714/1

(56) References Cited

U.S. PATENT DOCUMENTS

| | | | |
|---|---|---|---|
| 3,566,370 | * | 2/1971 | Worthington, Jr. et al. ..... 340/172.5 |
| 4,130,881 | * | 12/1978 | Haessler et al. ...................... 364/900 |
| 4,893,270 | * | 1/1990 | Beck et al. ............................ 364/900 |
| 4,975,840 | * | 12/1990 | De Tore et al. ...................... 364/401 |
| 5,235,510 | * | 8/1993 | Yamada et al. .................. 364/413.02 |
| 5,471,382 | * | 11/1995 | Tallman ............................... 600/300 |
| 5,492,117 | * | 2/1996 | Eisenberg et al. ................... 128/630 |
| 5,517,405 | * | 5/1996 | McAndrew et al. ................. 364/401 |
| 5,572,421 | * | 11/1996 | Altman et al. ....................... 395/203 |
| 5,594,637 | * | 1/1997 | Eisenberg et al. ................... 395/202 |
| 5,692,501 | * | 12/1997 | Minturn ............................... 128/630 |
| 5,796,759 | * | 8/1998 | Eisenberg et al. .................. 371/67.1 |
| 5,908,383 | * | 6/1999 | Brynjestad ........................... 600/300 |
| 5,937,387 | * | 8/1999 | Summerell et al. ...................... 705/2 |
| 5,974,124 | * | 10/1999 | Schlueter, Jr. et al. ......... 379/106.02 |
| 6,022,315 | * | 2/2000 | Iliff ...................................... 600/300 |
| 6,047,259 | * | 4/2000 | Campbell et al. ....................... 705/3 |
| 6,159,131 | * | 12/2000 | Pfeffer ..................................... 482/8 |

OTHER PUBLICATIONS

A computer protocol to predict myocardial infarction in emergency room department patients with chest pain NE Journal of Medicine, vol. 318, by L. Goldman et al, pp 792–833.

Risk Assessmant copied from Washington Post, Oct. 1, 1997.

Prevention of coronary heart disease with pravastatin in men with hypercholesterolemia J. Sheperd, et. al N.E. Journal of Medicine, vol. 333, Nov. 16, 1995 pp 1301–1306.

\* cited by examiner

Primary Examiner—Robert Beausoleil
Assistant Examiner—Bryce P. Bonzo
(74) Attorney, Agent, or Firm—Dickstein Shapiro Morin & Oshinsky LLP

(57) ABSTRACT

A computer system for performing an interactive assessment of the risk of an event, has a computer monitor to present to a user of the system a series of questions and potential responses, and a keyboard or other device to select a response to the question. The system can administer complex inverted tree type decision algorithms, in which the questions that are presented to the user, depend upon the response to the previous question, and an assessment of the risk of an event is presented to the user whenever they reach the terminus point in the decision tree. The risk assessment algorithm is data driven and a risk assessment is defined by entries in a file, which is available over a network. The system provides options so each user may view the path through the sequence of questions and answers, and interact with the risk assessment, in a manner customized for their own interactive session.

14 Claims, 21 Drawing Sheets

Fig. 5

| | Record | Definition | | |
|---|---|---|---|---|
| 511 → | 1 | Definition of risk to be assessed | | |
| 512 → | 2 | Source of risk decision rule | | |
| 513 → | 3 | Network location of risk definition file | | |
| 514 → | 4 | Max depth of risk decision tree | | |
| 515 → | 5 | Risk units | | |
| 516 → | 6 | Earliest date on which this risk assessment is valid | | |
| 517 → | 7 | Date after which this risk assessment is no longer valid | | |
| 518 → | 8 | E-mail address | | |
| 519 → | 9+ | | | |
| | No. | Field | Definition | Type |
| 520 → | 1 | NodeID | Unique node identifier (numeric) | Char |
| 521 → | 2 | PredNode | NodeID of the predecessor node | Char |
| 522 → | 3 | NodeName | Unique node name | Char |
| 523 → | 4 | NodeLevel | Level of node in decision tree | Integer |
| 524 → | 5 | NodePos | Vertical position of node in tree display | Integer |
| 525 → | 6 | NumAbove | Number of predecessor nodes | Integer |
| 526 → | 7 | NumBelow | Number of child nodes | Integer |
| 527 → | 8 | Question | Text of question | Char |
| 528 → | 9 | NodeLabel | Response associated with this NodeID | Char |
| 529 → | 10 | Risk | Risk value if a terminal node (NumBelow=0) | Char |
| 530 → | 11 | YoungestSib | Lowest NodeID of all nodes with this predecessor | Integer |
| 531 → | 12 | OldestSib | Highest NodeID of all nodes with this predecessor | Integer |

500 (top section), 501 (upper brace), 502 (lower brace)

601 → Myocardial Infarction in Emergency Department Patients with Chest Pain^

602 →  A Computer Protocol to Predict Myocardial Infarction in Emergency Department Patients with Chest Pain; New England Journal of Medicine; Vol 318, March 31, 1988, pp797-803^

603 → http://www.the4dgroup.com/RiskControl/myoinfarc.rsk^
604 → 8^
605 → risk of myocardial infarction^
606 → January 1, 1998^
607 → December 31, 1998^
608 → rsk@the4dgroup.com^

610 →  1^0^Node1^0^11^0^2^ST elevation or Q waves in 2 or more leads, not known to be old?^^^0^0^

612 → 2^1^Node2^1^9^1^2^Chest pain began >= 48 hours ago?^No^^2^3^
613 → 3^1^Node3^1^13^1^0^Hi risk^Yes^High risk^2^3^

4^2^Node4^2^6^1^2^Prior history of angina or MI?^No^.004^4^5^
5^2^Node5^2^11^1^2^ST-T changes of ischemia or strain, not kinow to be old?^Yes^.005^4^5^
6^4^Node6^3^3^1^2^ST-T changes of ischemia or strain, not known to be old?^Yes^0.0^6^7^
7^4^Node7^3^8^1^2^Pain radiates to neck or left shoulder or left arm?^No^0.0^6^7^
8^5^Node8^3^10^1^0^Lo risk^No^0.0^8^9^
9^5^Node9^3^12^1^0^Hi risk^Yes^0.0^8^9^
10^6^Node10^4^2^1^2^Longest pain episode >= 1 hour?^No^0.0^10^11^
11^6^Node11^4^4^1^0^Hi risk^ ^0.0^10^11^
12^7^Node12^4^6^1^2^Q12^F^0.0^12^13^
13^7^Node13^4^10^1^2^ Q13^F^0.0^12^13^
14^10^Node14^5^1^1^2^ Q14^F^0.0^14^15^
15^10^Node15^5^3^1^0^ Q15^Fo^0.0^14^15^
16^12^Node16^5^5^1^2^ Q16^F^0.0^16^17^
17^12^Node17^5^7^1^0^ Q17^F^0.0^16^17^
18^13^Node18^5^9^1^0^ Q18^F^0.0^18^19^
19^13^Node19^5^11^1^0^ Q19^F^0.0^18^19^
20^14^Node20^6^0^1^0^ Q20^F^0.0^20^21^
21^14^Node21^6^2^1^0^ Q21^F^0.0^20^21^
22^16^Node22^6^4^1^2^ Q22^F^0.0^22^23^
23^16^Node23^6^6^1^0^ Q23^F^0.0^22^23^
24^22^Node24^7^3^1^2^ Q24^F^0.0^24^25^
25^22^Node25^7^5^1^0^ Q25^F^0.0^24^25^
26^24^Node26^8^2^1^0^ Q26^F^0.0^26^27^
27^24^Node27^8^4^1^0^ Q27^F^0.0^26^27^

| No. | Field | Definition | Type | R/C |
|---|---|---|---|---|
| 1 | NodeID | Unique node identifier (numeric) | Char | R |
| 2 | PredNode | NodeID of the prdecessor node | Char | R |
| 3 | NodeName | Unique node name | Char | R |
| 4 | NodeLevel | Level of node in decision tree | Integer | R |
| 5 | NodePos | Vertical position of node in tree display | Integer | R |
| 6 | NumAbove | Number of predecessor nodes | Integer | R |
| 7 | NumBelow | Number of child nodes | Integer | R |
| 8 | Question | Text of question | Char | R |
| 9 | NodeLabel | Response associated with this NodeID | Char | R |
| 10 | Risk | Risk value if a terminal node (NumBelow=0) | Char | R |
| 11 | YoungestSib | Lowest NodeID of all nodes with this predecessor | Integer | R |
| 12 | OldestSib | Highest NodeID of all nodes with this predecessor | Integer | R |
| 13* | Display | Display node (Yes/No) | Boolean | C |
| 14* | BtnLeft | Position (left) of question button | Integer | C |
| 15* | BtnTop | Position (top) of question button | Integer | C |
| 16* | BtnWidth | Width of question button | Integer | C |
| 17* | BtnHeight | Height of question button | Integer | C |
| 18* | BtnMidPnt | MidPoint of question button | Integer | C |
| 19* | TextLeft | Postion (left) of response text | Integer | C |
| 20* | TextTop | Position (top) of response text | Integer | C |

700

710 — 1
711 — 2
712 — 3
713 — 4
714 — 5
715 — 6
716 — 7
717 — 8
718 — 9
719 — 10
720 — 11
721 — 12
740 — 13*
741 — 14*
742 — 15*
743 — 16*
744 — 17*
745 — 18*
746 — 19*
747 — 20*

| | |
|---|---|
| Fig. 15(a) | |
| Fig. 15(b) | |
| Fig. 15(c) | |
| Fig. 15(d) | |
| Fig. 15(e) | |

| State | Action | Program steps |
|---|---|---|
| START ←1510 | Initialize | • Initialize<br>• State = IDLE |
| IDLE ←1520 | Specify risk assessment | • Wait upon name of type of risk assessment<br>• If name is valid the<br>  • State= GET_RISKDEF<br>• Else<br>  • Msgbox "Illegal name"<br>  • State = IDLE |
| | Terminate assessment | • State=END |

| | | |
|---|---|---|
| 1530 — GET_RISKDEF | Get Risk Definition | • If there is a copy of the risk assessment on the client machine<br>  • Then retrieve local copy of risk definition<br>  • State=PARSE_RISKDEF<br>• If there is no copy of the risk assessment on the client then<br>  • Format request for risk assessment from server<br>  • Connect with the server<br>  • Request the risk assessment from the server<br>  • Wait and retrieve the response from the server<br>  • Disconnect with the server<br>• If the response is an errormsg then<br>  • Display error message<br>  • State = IDLE<br>• If the response is a risk definition file then<br>  • State = PARSE_RISKDEF |
| 1540 — PARSE_RISKDEF | Parse risk definition | • Read and process risk definition<br>• If no error then<br>  • Save RiskTree definition<br>  • SaveMaxDepth of RiskTree<br>  • State = INIT<br>• If there is an error then<br>  • Display error message<br>  • State = IDLE |

Fig. 15(d)

| | | |
|---|---|---|
| 1576 | Increase levels shown below | • If DisplayLevelsBelow<MaxDepth the MaxDepth=MaxDepth + 1<br>• DisplayRiskAssessment<br>• State=ADMIN_RISK |
| 1577 | Decrease levels shown below | • If DisplayLevelsBelow > 1 then MaxDepth=MaxDepth-1<br>• DisplayRiskAssessment<br>• State=ADMIN_RISK |
| 1578 | Change display mode | • If Display='Tree' then DisplayType='Text' else DisplayType = 'Tree'<br>• DisplayRiskAssessment<br>• State=ADMIN_RISK |
| 1579 | Prior Question | • Set CurrentQuestion = Previous Question<br>• DisplayDepth = DisplayDepth-1<br>• DisplayRiskAssessment<br>• State=ADMIN_RISK |
| 1580 | MouseOver Question icon | • While mouse is over question icon display full text of question in popup box<br>• State=ADMIN_RISK |
| 1581 | MouseOver Response icon | • While mouse is over response icon display full text of response in popup box<br>• State=ADMIN_RISK |

COMPUTER SYSTEM AND METHOD FOR A SELF ADMINISTERED RISK ASSESSMENT

BACKGROUND OF THE INVENTION

1. Field of the Invention

This invention relates to a computer system for a self administered assessment of the risk of an event, and more specifically, to a computer system and method for assessing the risk of an event based on responses to questions posed to a user through an interactive self administered risk assessment computer program.

2. Description of the Prior Art

The means to administer a risk assessment have not kept pace with the increasingly complex risk assessment rules that are the result of extensive research and analysis. Particularly in the area of health, data that is collected with the goal of understanding the factors associated with a medical condition, from expensive well-planned epidemiological research studies, may have been analyzed by means of logistic regression, regression trees, discriminant analyses, or other sophisticated statistical methodologies, that result in extremely complicated rules to assess risk. Such rules are too complex to be readily applied. This invention provides a means to allow even an unsophisticated user to perform highly complex risk assessments in a casual though error-free manner.

It is clear that such a tool is needed. For instance, the changing face of health care is, among other things, forcing people to take more responsibility for their own health, and assessing personal risk is an important facet. We see more instances of simple health assessments printed in newspapers, and magazines. By necessity these personal risk assessments must be easy for the reader to apply, since usage rates for complex assessments are low, and error rates are high. The typical personal assessment may require answering a simple set of questions, adding up a point total, and then assessing risk according to the range in which the point total falls. Such simple assessments are about at the level of complexity that can be typically handled without undue chance of error. The problem with such simple assessments is that they are by necessity simplifications from more detailed studies, and subsequently lack the precision of the studies from which they are taken. The tradeoff is that to be usable, they have to be simplified. The main object of the current invention is to provide a useable computer tool that can administer even the most sophisticated risk assessments.

Even sophisticated users may have difficulty performing a complex risk assessment. The research paper "A computer protocol to predict myocardial infarction in emergency department patients with chest pain", published in the New England Journal of Medicine, Mar. 31, 1988, Vol 318, pages 797–803, presents a risk assessment that can be used by emergency room medical personnel for triage of patients with symptoms of chest pain. The analysis and procedure is presented without any suggestion for a means by which it may be operationally used in the emergency room. The complexity of the decision rule, possibly requiring the answering of up to 8 questions, and the severity of the consequences should a mistake occur, mandate a careful approach to the means by which the rule is implemented. The present invention can be an important element in standard operation procedure by which this rule is applied in the emergency room.

OBJECT AND ADVANTAGES OF THE INVENTION

The main object of the present invention is a computer system that provides an easy means for a user to invoke and perform and interactive risk assessment. An important feature of the invention is the ease with which extremely complex risk assessment algorithms can be administered. This means that users of the invention will have access to, and be able to self administer risk assessments from research studies without having to be concerned with the complexities of the methodologies and implementation. Also risk assessments will no longer have to be simplified in order to be usable. The invention achieves this by administering an interactive risk assessment, which poses one question at a time, recording responses, and presenting to the user either the assessed risk, or the next portion of the risk assessment algorithm that they are to respond to. Also, the risk assessment program has the means to present the risk assessment in a multiplicity of formats, and with customization options to let the user proceed in a manner that they find most useful.

Another important object of the system is to be able to administer complex decision rules. This includes inverted tree type decision structures in which the path of questions is dependent and determined by the responses to prior questions. Such structures have been heretofore unavailable for personal risk assessments because of their complexity.

Other important objects of the invention are the wide availability of the system, the ease with which the risk assessment algorithm may be updated and maintained, as well as the scope of risk algorithms that can be available to users. Since the assessment is data driven from a risk assessment definition maintained on a server node of a computer network, all computers that have access to the server can be used to administer a risk assessment. Update of the risk assessment, as more current algorithms become available is achieved by replacing the risk assessment definition with the new definition and are immediately available in all subsequent risk assessments. Also, since any risk assessment that can be defined according to the structure of the risk definition file can be administered by the program, and this structure is general enough to accommodate a wide variety or risk decision structures, a large number of different risk assessments can be maintained in a central location on the same server and made available to users. An additional feature is that all these risk assessments are now administered in a similar way, so once the user can successfully master the administration of any risk assessment, they have the skills to administer all others.

In accordance then with the purpose of the invention, as embodied and broadly described herein, the invention consists of a client program running on a client node of a computer network, and a server program running on server nodes of a computer network. As a response to a request from the client program for a risk assessment definition, the server can send a response to the client program, that has sufficient information to fully describe the risk assessment that is to be administered. The system is thus data driven, and can administer any risk assessment that conforms to the structure and criteria of the risk definition file. Each risk definition is easily updateable by replacing the risk definition file with a new file that describe an updated risk assessment decision rule.

The system is capable of presenting in a fashion usable to even novice users, even the most complex risk assessments involving deeply nested decision paths, and paths in which the questions that is asked at any level is dependent upon the answer to previous questions, and can implement complicated mathematical risk assessment formulas, in which the values for parameters are provided by the responses to questions presented during the risk assessment.

The user interface of the risk assessment program is event driven, and carefully guides the user through the intricate risk assessment by presenting a series of questions to which the user in turn responds. At the end of a series of questions the risk assessment is presented to the user. The interaction between the user and the risk assessment client program include not just the ability to respond to questions on the screen, but also provide means for the user to customize the screen presentation in a manner consistent with their personal comfort level. A multiplicity of display modes are available, and the user may choose the display mode with which they are most comfortable, and during the risk assessment switch between display mode. Also, the degree of detail about the previously answered questions and subsequent questions that is displayed is controlled by the user.

Other objects and advantages of the invention will be set forth in part in the description which follows and in part will be obvious from the description or may be learned by practice of the invention. The objects and advantages of the invention will be realized and attained by means of the elements and combinations particularly pointed out in the appended claims.

BRIEF DESCRIPTION OF THE DRAWINGS

The accompanying drawings, which are incorporated in and constitute a part of the specification, illustrate the preferred embodiment of the invention, and together with the detailed description of the preferred embodiment, serve to explain the principles of the invention.

FIG. 5 is a file format for the risk definition file.

FIG. 6 is an example of the contents of the risk definition.

FIG. 7 is a data structure for maintaining information to administer and display an inverted tree decision rule.

DETAILED DESCRIPION OF THE PREFERRED EMBODIMENT

Figure 1:
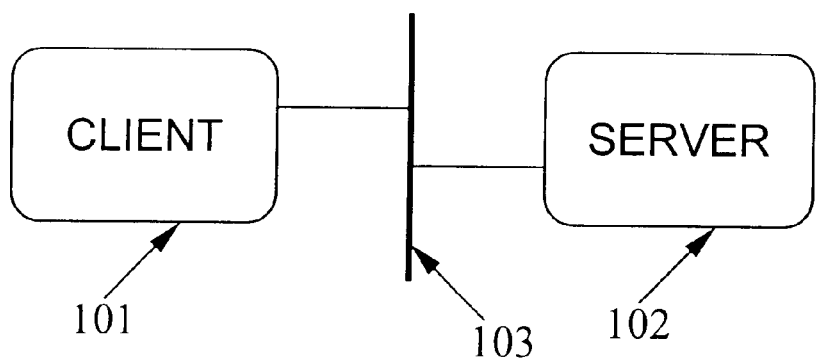
FIG. 1 is a block diagram of the preferred embodiment of the present invention.

References will now be made in detail to the preferred embodiments of the invention, examples of which are illustrated in the accompanying drawings. Wherever possible, the same reference numbers will be used throughout the drawings to refer to the same or like parts.

1. Definitions and Overview

Before discussing the preferred embodiment of the invention it will be helpful to define certain terms which are used in the disclosure.

A risk assessment is a set of steps that is used to assess the risk of an event. The risk assessment may be presented quantitatively as in the expected number of deaths per 100,000 population, or may be qualitative resulting in an assessment such as 'High risk' of acute myocardial infarction.

The term risktree-client program refers to a computer program running on a computer attached to a computer network, and is a client-node on the computer network. All interactions by the user to perform the risk assessment take place between the user and the risktree-client program.

The term risktree-server program refers to a computer program running on a computer attached to a computer network, and is a server-node on the computer network. The risktree-server program responds to requests from a risktree-client program for the information to administer a risk assessment by sending all the information that is required for the risktree-client to administer the risk assessment.

The term risk definition or risk definition file refers to the information that is maintained on the risktree-server, and which provides sufficient information for the risktree-client to fully administer a risk assessment.

This system can accommodate risk assessment decision rules that follow a complex inverted tree decision structure. An inverted tree decision structure starts with a single initial question to which the user may respond. Depending on the user's response, the risk assessment may terminate with an assessment of the risk or may proceed to another question to which the user must respond, with this process continuing until the decision procedure terminates with sufficient information to calculate and present the risk assessment. Importantly, each 'next' question in the risk assessment depends only on the response to the previous question, and different questions may be asked depending on the different responses to a question.

This invention then is a computer system for providing an interactive risk assessment of an event occurring. The system partitions the operation of the system between a risktree-client program which is the program that the user interacts with to perform the risk assessment, and a risk-Tree server program that stores and provides the risk definition file that defines the risk assessment. The risktree-client program administers a risk assessment that is defined entirely by the information in the risk definition file. All communication between the risktree-client and risktree-server use a non-persistent network connection maintained only for the duration of the transaction.

2. A System and Method for Accessing Medical Information Over a Network

A. Hardware, Operating System and Application Development Software

FIG. 1 is a block diagram of the preferred embodiment of the present invention. A system 100 of FIG. 1 illustrates the risktree-client computer 101, the risktree-server computer 102, and the network interface 103 over which they establish a connection. In the preferred embodiment the network interface protocol that is used is the industry standard network protocol TCP/IP.

Figure 2:
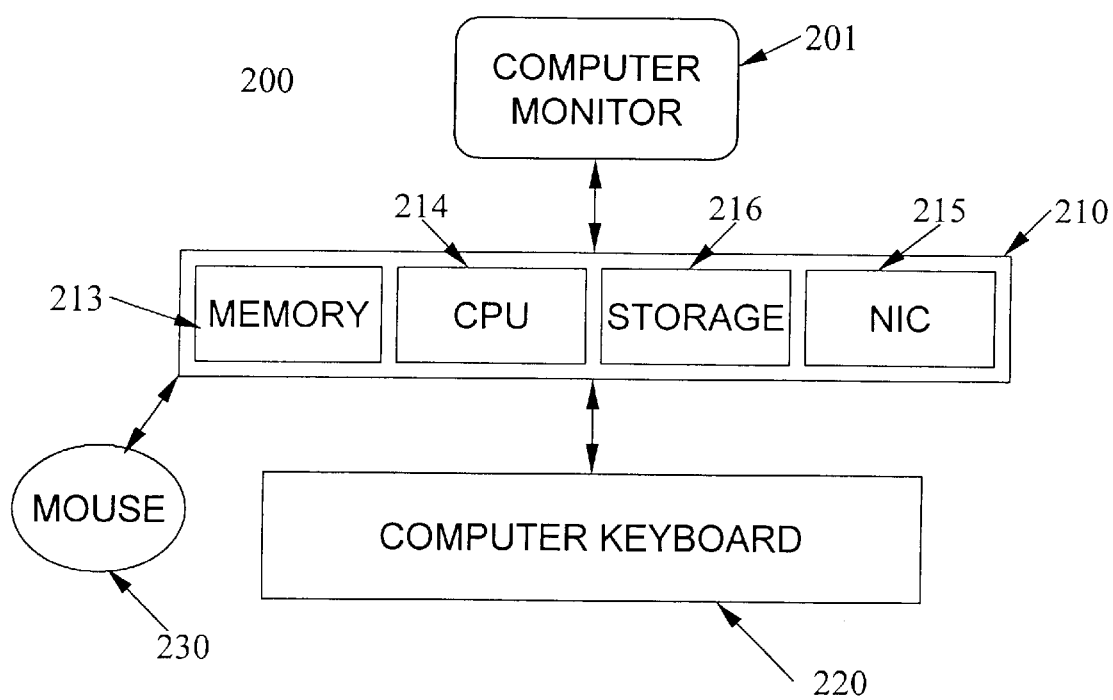
FIG. 2 is a block diagram of client program of FIG. 1.

FIG. 2. is a block diagram of the risktree-client computer 101. In the preferred embodiment the system 200 consists of a computer monitor 201, a computer 110, a computer mouse 230, and a computer keyboard 220. The computer 210 includes a memory 213 and a processor (CPU) 214, a mass storage device 216, and a network interface card (NIC) 215. Monitor 201, the computer mouse 230, and computer keyboard 220, are connected to computer 210 in a manner known to persons of ordinary skill in the art.

Computer 210 preferably is a Dell OptiPlex XMT, the keyboard 220 is a Dell Quietkey, and monitor 201 a Dell Ultrascan 17XE, all manufactured by the Dell Corporation of Austin, Tex. The NIC 215, is an Intel EtherExpress 16, 16-bit ISA ethernet Adapter card manufactured by the Intel Corporation of Santa Clara, Calif. The computer mouse 230, is a Microsoft System Mouse, manufactured by the Microsoft Corporation of Redmond, Wash.

In the preferred embodiment, computer 210 is executing under Microsoft Windows 95. The client program is written in a computer language called Microsoft Visual Basic using the Microsoft Visual Basic Version 5.0. This application development tool is from the Microsoft Corporation of Redmond, Wash. Other embodiments may use other hardware and software components.

Figure 3:
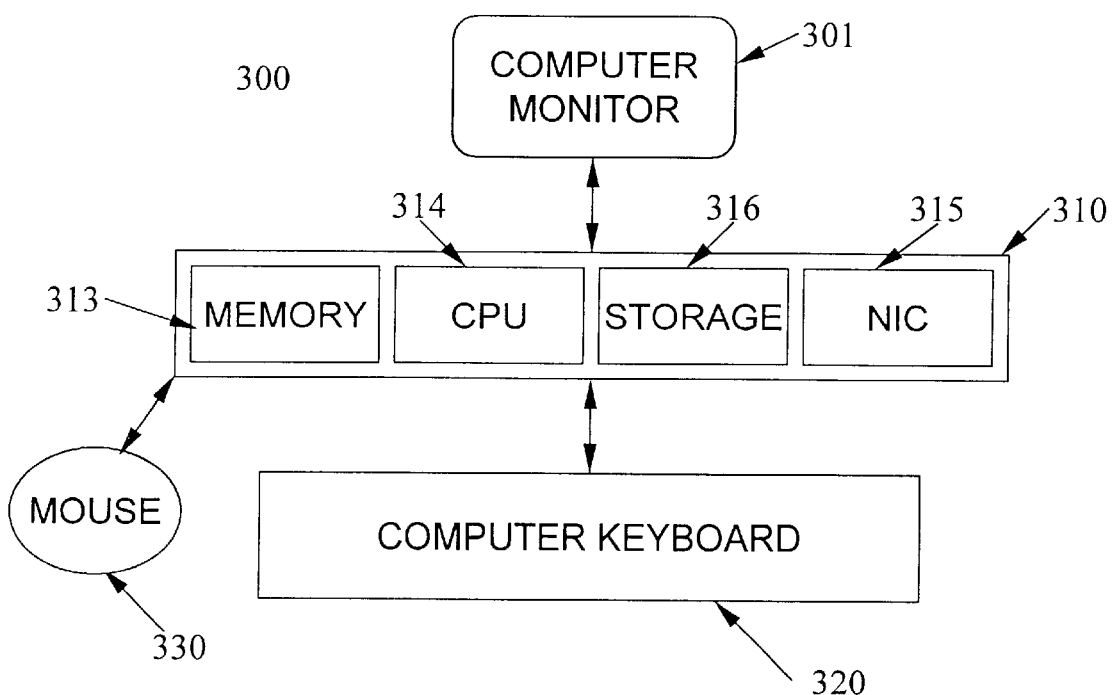
FIG. 3 is a block diagram of the server program of FIG. 1.

FIG. 3. is a block diagram of the risktree-server computer 102. In the preferred embodiment the system 300 consists of a computer monitor 301, a computer 310, a computer mouse 330, and a computer keyboard 320. The computer 310 includes a memory 313 and a processor (CPU) 314, a mass storage device 316, and a network interface card (NIC) 315. Monitor 301, the computer mouse 330, and computer keyboard 320, are connected to computer 310 in a manner known to persons of ordinary skill in the art.

Computer 310 preferably is a Dell OptiPlex XMT, the keyboard 320 is a Dell Quietkey, and monitor 301 a Dell Ultrascan 17XE, all manufactured by the Dell Corporation of Austin, Tex. The NIC 315, is an Intel EtherExpress 16, 16-bit ISA ethernet Adapter card manufactured by the Intel Corporation of Santa Clara, Calif. The computer mouse 330, is a Microsoft System Mouse, manufactured by the Microsoft Corporation of Redmond, Wash.

In the preferred embodiment, computer 310 is executing under Microsoft Windows NT Server 4.0, and is running the Microsoft Internet Information Server, both manufactured by the Microsoft Corporation of Redmond, Wash. Other embodiments may use other hardware and software components. The risk definition files are stored on the risk-server and are accessed by the risktree-client using the industry standard hypertext transport protocol.

B. Risk assessment example

Figure 4A:
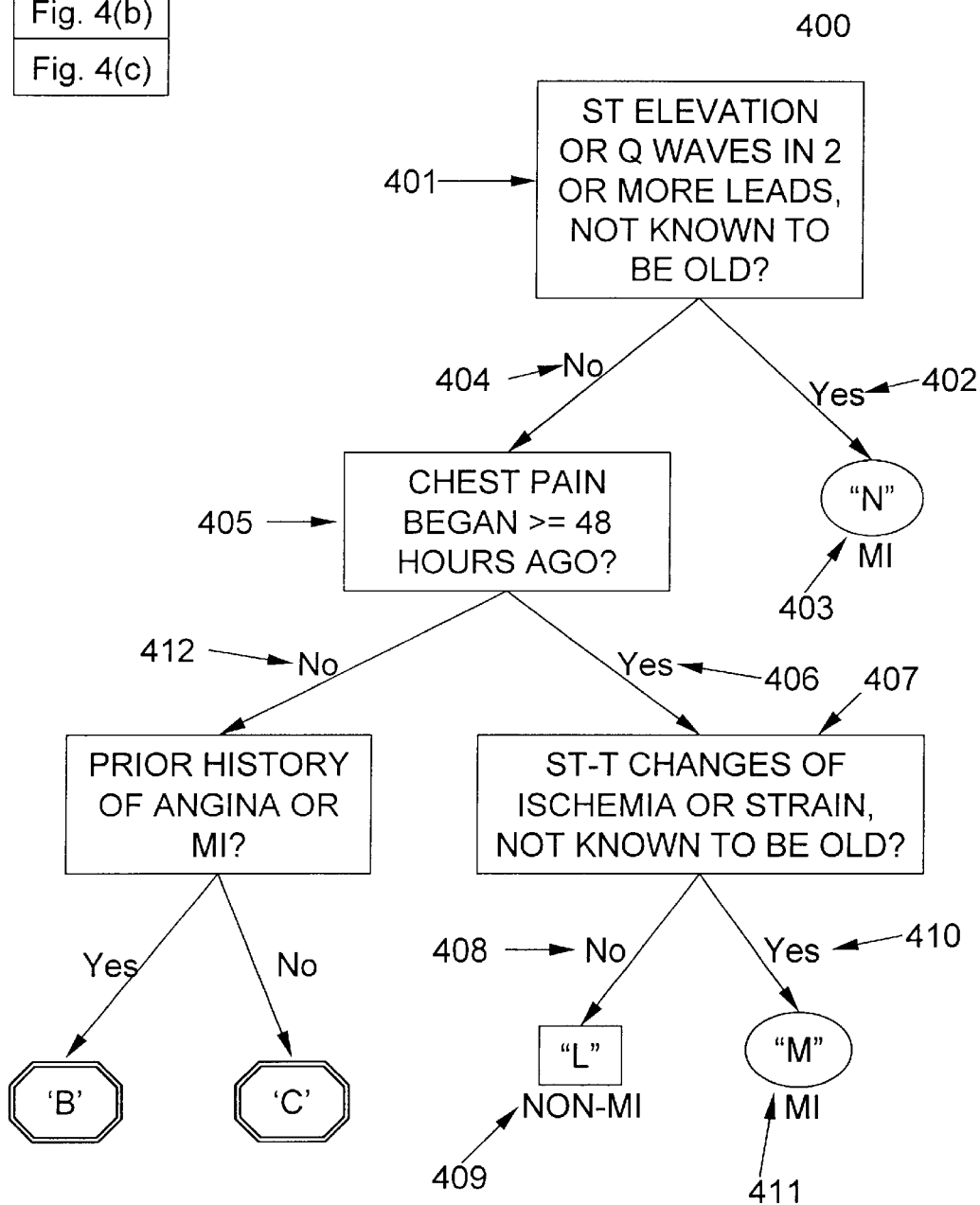
FIG. 4 is an example of risk assessment decision rule.
Figure 4B:
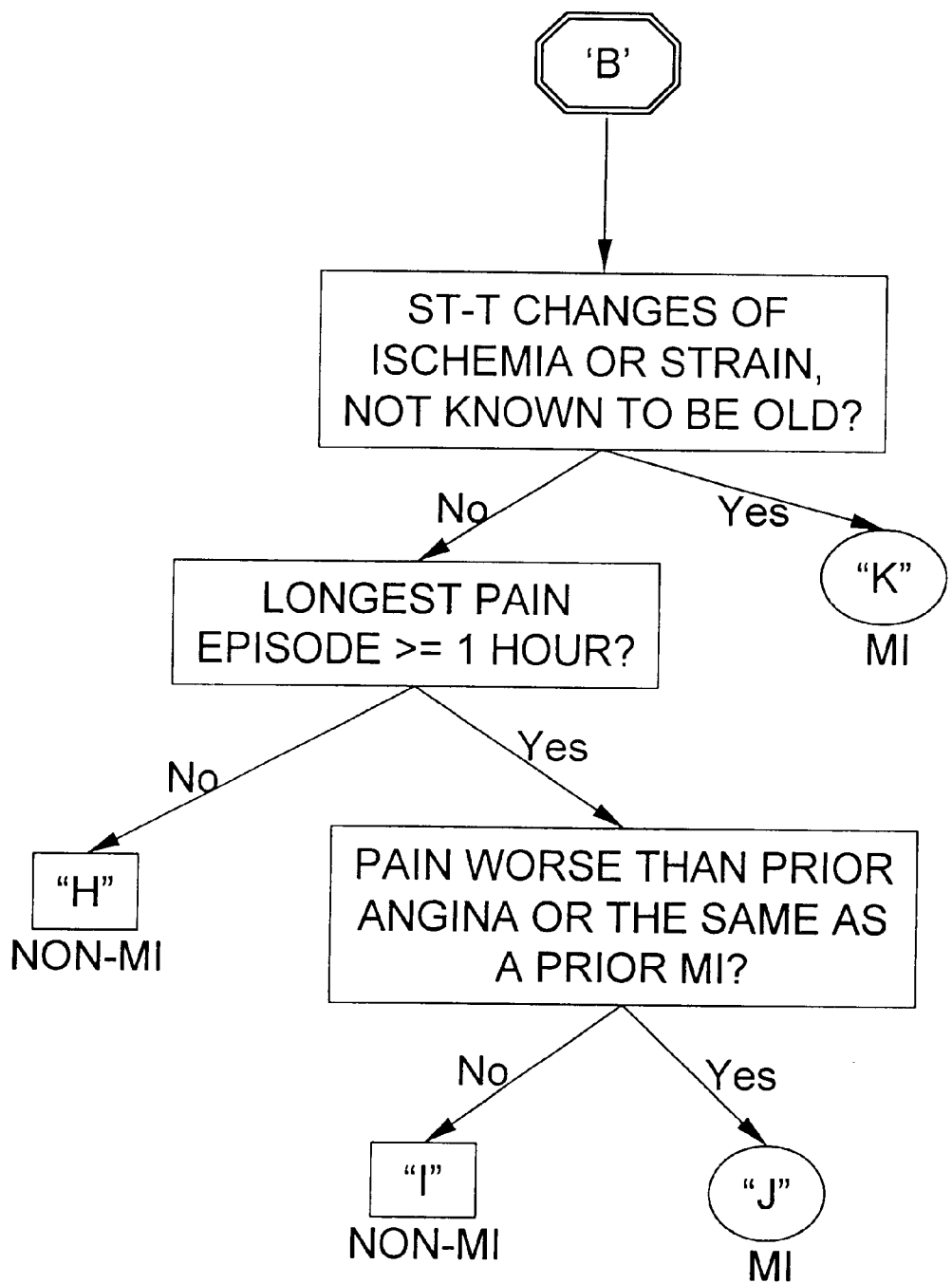
Figure 4C:
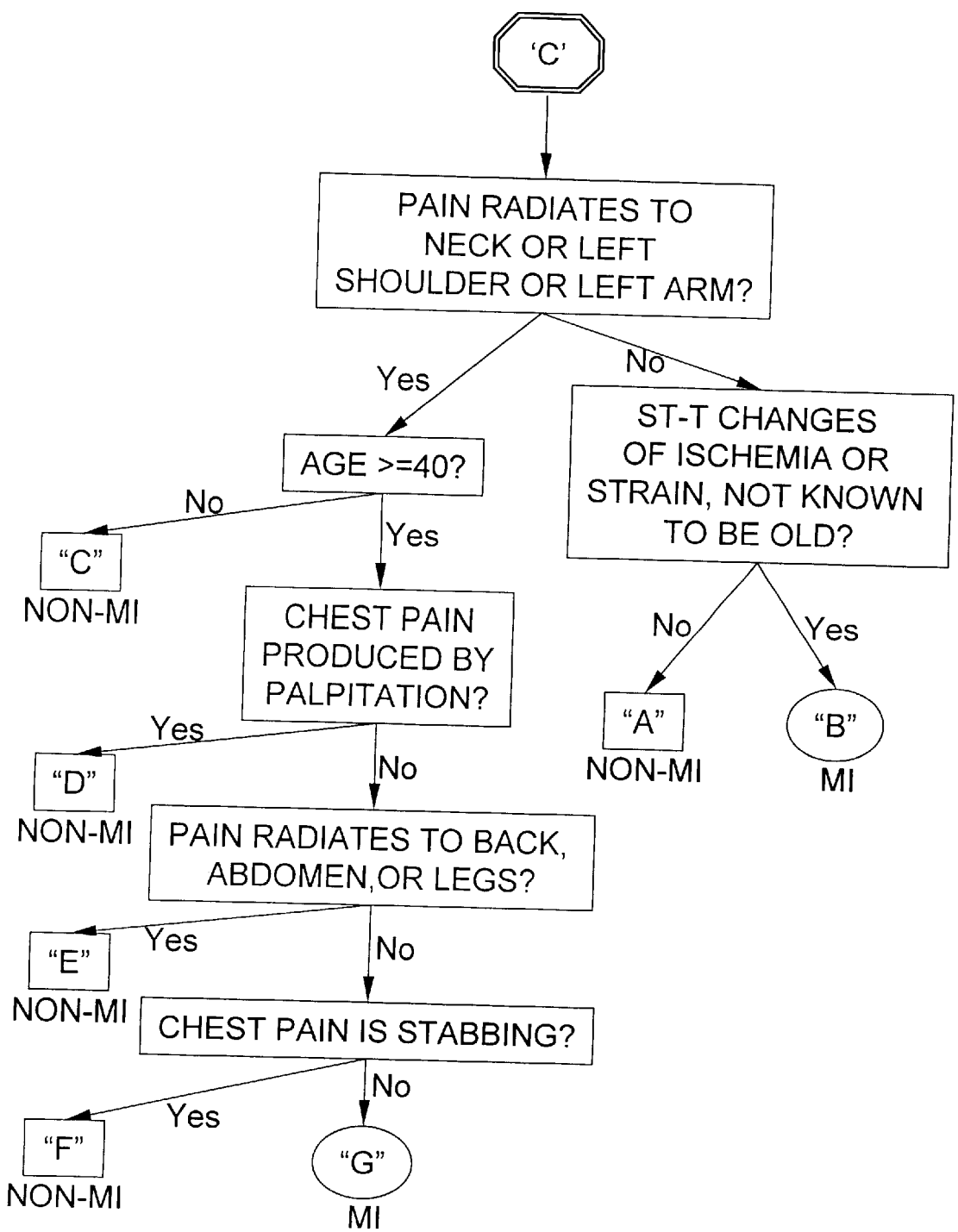

FIG. 4. is a specifi example 400 of a complicated inverted tree risk assessment decision rule that the system can handle. The system is not limited to this specific risk assessment, and the example is only used as it will be useful in explaining the operation of the preferred embodiment. This example is taken from an article 'A computer protocol to predict myocardial infarction in emergency department patients with chest pain, by L. Goldman et. al., published in the New England Journal of Medicine, Volume 318, Number 13, on Mar. 31, 1988, pages 797–803. The article presents a risk assessment rule for predicting whether a patient admitted to an emergency room with chest pain has a low or high risk for the presence of myocardial infarction. It is a complicated inverted tree decision rule that is difficult to administer without assistance from some kind of tool.

The first question in the decision rule 401, asks the question 'ST elevation or Q waves in 2 or more leads, not known to be old?.' If the answer to this question is Yes 402, then the risk assessment is over and there is a 'Hi' risk 403 that the patient has had a myocardial infarction. If however, the answer is 'No' 404 then the risk assessment proceeds by asking the next question 405 'Chest pain began more than 48 hours ago?.' If the answer to this question is 'Yes' 406, then the risk assessment proceeds to the question 407 'ST-T changes of ischemia or strain, not known to be old?' If the response to this question is 'No' 408, then the risk assessment is over and there is a 'Lo' risk 409 that the patient has had a myocardial infarction. If the answer however to question 407 is 'Yes' 410, then the risk assessment is terminated by categorizing the patient as having a 'Hi' risk 411 of having had a myocardial infarction.

If the answer to question 405 is 'No' 412, then the risk assessment proceeds by asking the question 413 'Prior history of angina or MI?', and may proceed through as many as 5 more levels of questions before arriving at the assessment of risk.

All subsequent questions in the risk assessment are operationally evaluated during the process of performing the risk assessment in a manner analogous to that described above. If the user has arrived at the bottom of a branch of the risk assessment tree, then the risk assessment has been completed and the risk can be evaluated and reported. If the user is not at the bottom of the tree then the question has to be considered by the user, and a selection made from the valid responses.

C. Data Structures

FIG. 5 shows the structure 500 of the risk definition file that describes the risk definition that is maintained on the risktree-server 300 of FIG. 3. Every risk assessment that can be defined according to this structure can be displayed and administered by the risktree-client program. The first eight records 501 of the risk definition provide information about the type of risk assessment. All subsequent records 502 after the eighth record have a similar format and fully describe the content and structure of the questions and responses for the risk assessment, and have one record for each node of the decision rule.

Record one 511 of the risk definition file provides a definition of the risk that is to be assessed. The second record 512 provides the authoritative reference for the risk assessment. Record three 513 is the network location of the risk definition file, and in the case of the preferred embodiment is the Uniform Resource Location (URL) providing the internet address of the risk definition file. The fourth record 514 provides the maximum depth of the tree structure. This information is used by the risktree-client to display and store the risk definition. The fifth record 515 gives the risk units that will be displayed with the risk assessment. For instance, if the risk assessment calculates a mortality value the risk units might be 'per 100,000 population.

Since risk assessments may pertain to life threatening decisions or other important decision record six 516 and record seven 517 provide dates that bound a period of time during which it is valid to use the decision rule. Record six 516 provides a start date in month-day-year format after which the decision rule may be used, and record seven 517 provides an end date in month-day-year format after which the risk assessment should not be used. The eighth record 518 provides an internet E-mail address as a contact for further information or questions about the specific risk assessment.

Following the eighth record are a set of records called node-descriptor records 519 that all have the same format and describe the nodes of the inverted tree structure, the relationship between the nodes, and the associated risk. There will be one entry for each node. In the example FIG. 4. 400 of an inverted tree structure for an assessment of the risk of myocardial infarction there are 27 boxes. The risk definition file for that risk assessment would then have 27 node-descriptor records 519. The risk definition file corresponds to the rule to assess the risk of myocardial infarction in FIG. 4, and is presented in FIG. 6.

There are 3 types of nodes in an inverted tree; a start node, question/response node, and terminal nodes. A start node is the first question in the risk assessment, and in the case of FIG. 4 is the identified with the question 401 'ST elevation or Q waves in 2 or more leads, not known to be old?' A question/response node is one that identifies the prior node or immediate predecessor question, the response to the prior question that leads to the node, and the new question associated with the node. In the case of FIG. 4, box 405 is an example of a question/response node with the arrow 404 indicating the prior question was 401, the response was 'No' 404, and the new question that will be asked 405 is 'Chest pain began more than 48 hours ago?' A terminal node is one that identifies the prior node or immediate predecessor question, the response to the prior question that leads to the terminal node, and the risk assessment. In the case of FIG. 4, box 403 is an example of a terminal node with the arrow 402 indicating the prior question was 401, the response was 'Yes' 402, and the risk assessment is 'Hi' 403 risk of myocardial infarction.

There are 12 fields in the node-descriptor 519 that give all the information necessary to describe each of the types of nodes in the inverted tree decision structure. Field 'NodeID' 520 provides a unique identifier for the Node. In the preferred system the NodeIDs are numbered sequentially top-down and left-to-right starting at '1'. The NodeID is in character format and the node with NodeID '1' is always the start node in the risk assessment. Field 'PredNode' 521 provides the NodeID 520 of the prior or predecessor node. In the case of the start node where there is no predecessor, and this value is blank. Field NodeName 522 provides a unique name for the risk description node, and is an alternate identifier to that of the NodeID 520 by which a node may be uniquely identified. Field 'NodeLevel' 523 gives a numeric value for the level of the node. The level is the number of questions that the user would have to respond to, in order to reach the current node. The start node is at Nodelevel '0'. In FIG. 4, the question in the box 405 is at Nodelevel '1', the question in the box 407 is at Nodelevel '2', and the risk assessment 403 is at NodeLevel '1'.

The field 'NodePos' 524 provides a numeric value with vertical positioning information that will be used by the risktree-client program to give a relative position that the program will use to display the node. Any 2 nodes with the same value of NodePos will be display with the same vertical alignment by the risktree-client program. The field 'NumAbove' 525 provides a numeric value with the number of predecessor nodes. For an inverted tree rule this will always have the value of '1', though for other types of decision structures that the system can handle, there may be more than a single path leading to the current node. In the case of the start node this value is 0. The field 'NumBelow' 526 gives a numeric value with the number of child nodes. In the case of a terminal node, this value will be '0'.

The field 'Question' 527 gives the text of the question that will be asked and is a character value of length up to 255 characters. In FIG. 4 the box 405 asks the question 'Chest pain began more than 48 hours ago?', and this value is found in the 'Question' field 527. The field 'NodeLabel' 528 is a character value of length up to 32 characters and gives the text of the response associated with the current node. In FIG. 4 one navigates to the box 405 by answering 'No' to the prior question 401, and in this example it is this value 'No' that is found in the 'NodeLabel' field 528. Field 'Risk' 529 contains a character representation of the risk that will be displayed whenever one reaches a terminal node. In FIG. 4 box 403 is a terminal node associated with 'Hi risk' risk of myocardial infarction, and it is the value 'Hi' that is found in the field 'Risk' 529. When displaying the risk for a terminal node in FIG. 4, the assessed value, in this case 'Hi risk', is combined with the 'Risk units' field 'of myocardial infarction' to provide the risk assessment that is presented to the user—'Hi risk of myocardial infarction'. The field 'YoungestSib' 530 gives the 'NodeID' 520 of the lowest numbered NodeID of all nodes that have the current node as a predecessor, and the field 'OldestSib' 531 gives the 'NodeID' 520 of the highest numbered NodeID of all nodes tht have the current node as a predecessor. These values are used by the risktree-client to display the paths between nodes.

In the preferred embodiment the fields 'NodeLevel', 'NodePos', 'NumAbove', 'NumBelow','YoungestSib' and 'OldestSib' are provided in the risk definition file, but in other embodiments they may all be calculated from the fields 'NodeID', and 'PredNode'.

FIG. 6 is a listing 600 of the risk definition for the example of the risk assessment to predict myocardial infarction in emergency department patients with chest pain of FIG. 4. It is to be understood that the risktree-client can display and administer any risk assessment, not just the assessment of myocardial infarction in emergency room department patients with chest pain, as long as the risk definition file follows the schema given in FIG. 5. In the risk definition file a caret '^' is used as a delimiter for records and fields, and can never occur as the content of an entry in the file.

The first line 601 'Myocardial infarction in Emergency Department Patients with Chest Pain' is an example of the Record 1 511 of FIG. 5. This information is displayed in the risk assessment display 810 of FIG. 8. The second line 602 is an example of the 'Source of the decision rule' 512, and gives the journal reference from which the risk assessment was coded, or it may be some other authoritative reference for the risk assessment. The third line 603 is an example of the 'Network location of risk definition file' 513 and gives the URL of the internet resource for the myocardial infarction risk definition file. The fourth line 604 gives is an example of the 'Max depth of the risk decision tree' 514, showing that for the myocardial infarction risk assessment the maximum depth of a risk assessment is 8 levels of questions and responses. The fifth line 605 is an example of the 'Risk units' 515 showing that for the myocardial infarction risk assessment the risk assessment will be displayed with the units 'of myocardial infarction' appended to the assessment. The myocardial infarction risk assessment always results in a decision that the patient has either 'High risk' in which case the risktree-client displays the assessed risk as 'High risk of myocardial infarction', or 'Low risk' in which case the risktree-client displays the assessed risk as 'Low risk of myocardial infarction.'

The sixth line 607 and seventh line 608 are examples of the dates 516 and 517 that bound the period of time during which the myocardial infarction risk assessment is valid. It shows a start date 'Jan. 1, 1998' before which the risk assessment should not be used and an end date of 'Dec. 31, 1998' after which this risk assessment should not be used. If the date on which the risk assessment is being performed is not within these bounds then the risktree-client will display a message 'Risk assessment out of date' and will not administer the risk assessment. This feature assures that the risk assessment must be reassessed on a timely basis. The eighth line 608 is an example of the 'E-mail address' 518, and provides a contact point for more information about the risk assessment. The information in lines 601, 602, 603, 606, 607, and 608 are displayed in a popup risk assessment information box that the user may access from the risk assessment display screen of FIG. 8.

The information in the set of lines 610, correspond to the entries that fully define the myocardial infarction risk assessment of FIG. 4. There are 27 lines in the set, one for each of the 27 boxes in FIG. 4, which represent either a start node, question/response node, or terminal node risk assessment. Each line of the set follows the structure of the node-descriptor 519. Line 611 is the start node for the myocardial risk assessment, line 612 a question/response node, and line 613 a terminal risk assessment node. All of the remaining 24 lines of the set 610 are either question/response nodes or terminal risk assessment nodes.

Line 611 describes the first question in the myocardial risk assessment of FIG. 4. There are 12 entries on this line each delimited by a caret '^' sign, and correspond to the structure of the node-descriptor 519. The 'NodeID' 520 is '1' and indicates that this is the start node or first qusestion in the risk assessment. The 'PredNode' 521 is '0' and identifies that the start node does not have a predecessor—it is the start of the risk assessment procedure. The 'NodeName' 522 is 'Node1' and is an alternative unique identifier for the node. The 'NodeLevel' 523 is '0' since this is the first question of the risk assessment and no questions have yet been answered. The 'NodePos' 524 is '11' and gives the relative vertical position when the node is displayed on the risk assessment display screen. Any node with a value of 'Node-Pos' less than '11' will always be displayed to its left; a node with a value of 'NodePos' equal to '11' will always be displayed under it, and a node with a value of 'NodePos' greater than 11 will be displayed to its right. The 'NumAbove' 525 is '0' since there are no nodes above the start node, and the 'NumBelow1 526 is '2' since there are 2 child nodes 405 and 403 of FIG. 4 which are defined by the lines in the risk defintion 612 and 613 respectively. The 'Question' 527 entry has the full text of the question for the corresponding node, in this case 'ST elevation or Q waves in 2 or more leads, not known to be old?.' The 'NodeLabel' 528 is blank since this is the first node in the risk assessment. For every other node it would have the full text of the question that led to this node from the question identified by 'PredNode 522. For instance for 612 the entry for 'NodeLabel' is 'No' indicating that this node followed as the answer to the first question in the risk assessment. The 'Risk' 529 is blank since this is not a terminal node in the risk assessment. For every terminal node this field will contain the value of the risk assessment. For instance, for 613 the entry for 'Risk' is 'High risk', indicating that if the user responded to the first question in the risk assessment by choosing the response 'Yes', then the risk assessment would be finished and the patient would be categorized as having a 'High risk of myocardial infarction.' The 'YoungestSib' 530 and 'OldestSib' 531 entries are '1' and '1' respectively because this is the first node in the risk assessment. For 612 the 'YoungestSib' and 'OldestSib' values are '2' and '3' indicating the range of 'NodeID's that identify all nodes that are responses to the same question—in this case that the nodes identified with NodeIDs '2' and '3' are both responses to the same question in the risk assessment. The 'YoungestSib' and 'OldestSib' entries for 613 are the same as for 612, since both identify nodes that are responses to the same question.

FIG. 7 shows the structure 700 of the risktree data structure that is used by the risktree-client to display and administer the risk assessment. This data structure is saved in the computer memory and is specific for each risk definition. In the preferred embodiment the risktree data structure is stored as a collection object. For the example of the myocardial infarction risk assessment of FIG. 4, there are 27 entries in the collection, one for each of the nodes of the myocardial infarction risk assessment decision tree.

The first 12 fields of the risktree data structure, 'NodeID' 710, 'PredNode' 711, 'NodeName' 712, 'NodeLevel' 713, 'NodePos' 714, 'NumAbove' 715, 'NumBelow' 716, 'Question' 717, 'NodeLabel' 718, 'Risk' 719, 'YoungestSib' 720, and 'OldestSib' 721' have exactly the same definition as the first 12 fields 520–531 in the definition of the node-descriptor 519 for FIG. 5. The values for these fields are taken directly from the risk definition files and saved in the collection. In the example of the myocardial risk assessment of FIG. 4, the nodes in the decision tree, which are coded as 27 separate records 610 in the risk definition file of FIG. 6, are saved in the risktree data structure as 27 elements in the collection.

The remaining 8 fields of the risktree data structure are calculated and provide the information that is needed to display the nodes of the tree in 'Tree' display mode. Field 'Display' 740 is a boolean field that determines whether a node will be displayed. For the preferred embodiment of the invention, the nodes that are displayed depend on the level of the current question and the number of levels above and below the current question that are to be displayed. For instance if the risk assessment is at the first question (level= 0), and the user has chosen to display 3 levels below the current question, then all nodes that have a 'NodeLevel' values of 0, 1, 2, and 3 will be displayed, and any values with a 'NodeLevel' with a value greater than '3' will not be displayed. In this case, the boolean field 'Display' will be set to 'True' for each node that is to be displayed and to ° False' for each node that is not to be displayed. As another example, if the current question is a node that is at level 3 of the risk assessment decision tree, and the number of levels to be displayed above the current question is set to '1', and the number of levels to be displayed below the current question is set to '1', then just the nodes that have a 'NodeLevel' value or 2, 3, or 4 will have their 'Display' value set to true. The values of 'Display' are recalculated just prior to every redrawing of the risk assessment decision tree on the display monitor. The display is redrawn whenever a response is selected to a question, or a change is made to either of the values for number of levels above or below the current node that are to be displayed.

For each node, the fields 'BtnLeft' 741, 'BtnTop' 742, BtnWidth' 743, and 'BtnHeight' 744 provide the top left, top width and height of the rectangle that is used to display the associated node on the display monitor. These values are recalculated just prior to every redrawing of the risk assessment decision tree on the display monitor. The values are calculated by taking into account the size of the display area and the nodes that are to be displayed. If the number of levels that are to be displayed is given by 'nLevel', the lowest value for a level that is to be displayed is given by the value 'lLevel', and the height of the display area is given by 'DisplayHeight', then the height of the node rectangle 'BtnHeight' value is calculated as 'DisplayHeight'/ (2*nLevel). The 'BtnTop' value is calculated as 'BtnHeight'/2+2*' ('NodeLevel'−lLevel).

By scanning the nodes for all levels that are to be displayed we can find the smallest and largest of the values of 'NodePos', the vertical positioning of the nodes to be displayed. These are denoted as 'smallPos' and 'largePos' respectively, and then calculate the value 'nPos'= 'largePos'−'smallPos'+1. If the width of the display area is given by 'DisplayWidth', then the width of the node rectangle 'BtnWidth' is calculated as 'DisplayWidth'/(2*nPos). The 'BtnLeft' value is calculated as 'BtnWidth'/2+ 2'BtnWidth'*('NodePos'−'smallPos'). These values are also recalculated just prior to every redrawing of the risk assessment decision tree on the display monitor.

For each node, the fields 'BtnMidPnt' 745 is calculated. This is the x-coordinate of the vertical line that is drawn above a node to show the user what question came prior to the current question, and the x-coordinate of the vertical line that is drawn below a node to show the user what question(s) follow a response to the current question. The value for 'BtnMidPnt' is calculated as ('BtnWidth'+'BtnLeft')/2, and is recalculated just prior to every redrawing of the risk assessment decision tree on the display monitor.

For each node, the fields 'TextLeft' 746, and 'TextTop' 747 provide the top left and top respectively of the text of the response that is displayed on the display monitor. The response is positioned just above and to the left of the center of the rectangle displaying the node. The values are calculated by as 'TextLeft'='BtnMidPnt'+50, and 'TextTop'= 'BtnTop'−25. The value is recalculated just prior to every redrawing of the risk assessment decision tree on the display monitor.

These values 741–747 provide sufficient information to redraw all the lines connecting the nodes in a 'Tree' display.

D. Risk assessment display

Figure 8:
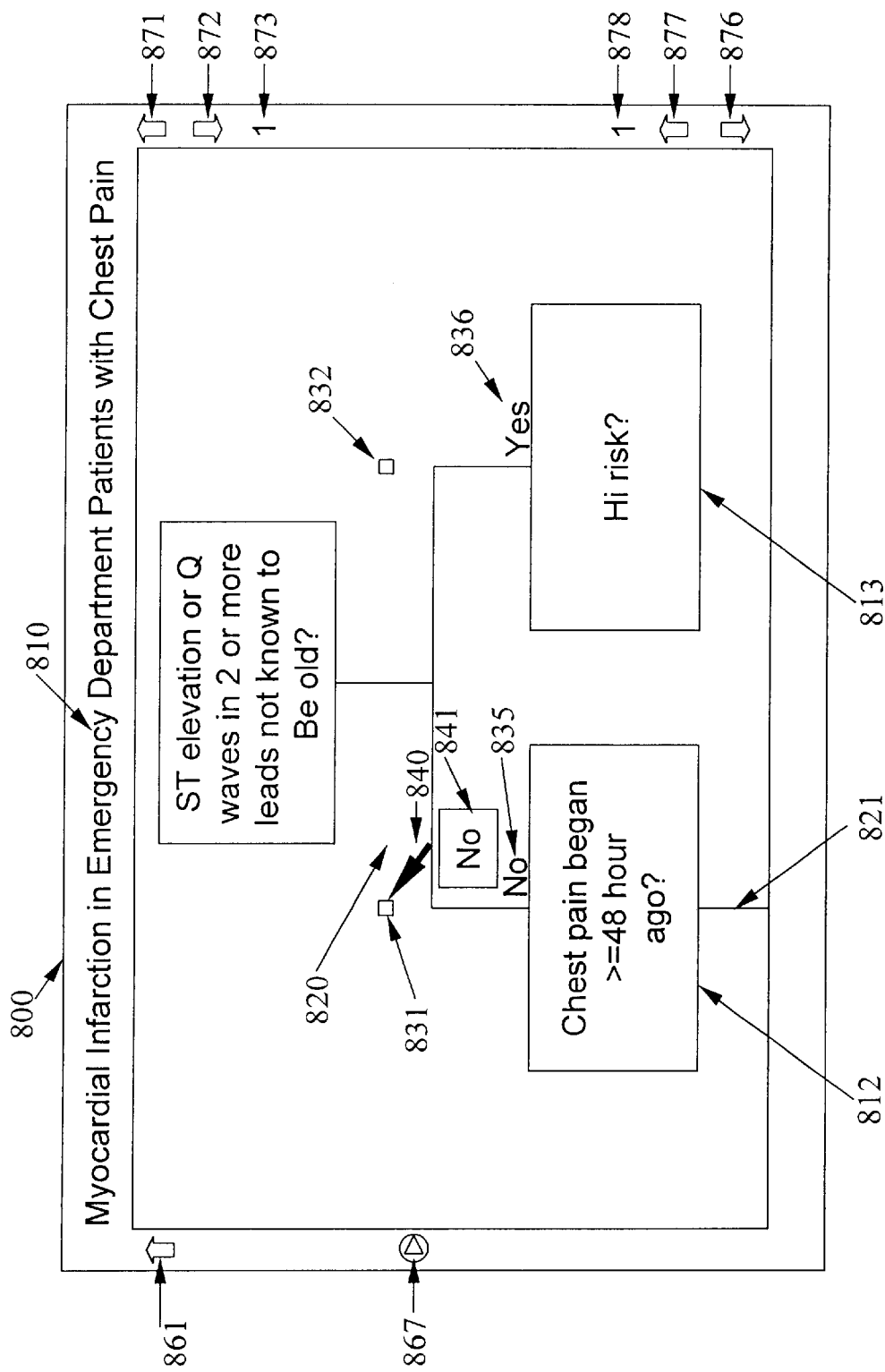
FIG. 8 is an example of a risk assessment screen showing the initial display of the risk assessment decision rule in tree display format.

FIG. 8 shows the main display 800 of the risktree-client at the beginning of the assessment for the risk of myocardial infarction in emergency department patients with chest pain, that was given in FIG. 4 The display shows the screen of the computer monitor 201 of the risktree-client 200. In this case the current a question is the first question in the risk assessment.

A title box 810 at the top of the computer monitor of the risktree-client identifies the type of risk that is being assessed; 'Myocardial Infarction in Emergency Department Patients with Chest Pain' as given in record 1 of the risk definition file. Three questions 811, 812, 813 are displayed on the screen. The question associated with the start node 811 'ST elevation or Q waves in 2 or more leads, not known to be old?' is at the top of the screen. The node 812 'Chest pain began more than 48 hours ago?' is a child node of question 821 associated with the response 'No', and node 813 'Hi risk' is a terminal node of question 821 associated with the response 'Yes'. The question buttons 811 and 812 are shaded darker than the terminal node 813 so they may be more readily distinguished. The question 811 is highlighted with a darker border to indicate to the user that it is the current question.

The lines 820 connect the nodes and clearly show the relationship between the questions displayed on the screen. Question 821 has no line above it indicating that it is a start node. The line 821 leads from question 812 and appears to go right off the screen, indicating that there are more questions lbelow that have not been displayed. That question 813 does not have a line leading down to another question indicating that it is a terminal node.

The small boxes 831 and 832 are associated with the responses 'No' 835 and 'Yes' 836 respectively to question 811. The screen cursor 840 is pointing directly at the small box and the boxed text 'No' 841 is a popup tooltip text that may contain a more complete description of response 'No' 831 to the associated question. This tooltip 841 text is only visible when the cursor is pointing directly in the small box response area.

Along the left edge of the screen are two icons. The 'Restart' icon 861 will be used to restart the risk evaluation over at the start node, and the 'Switch Display Context' icon 862 is used to switch the risk evaluation to 'Text' display, but maintaining the same position in the risk assessment.

Along the right edge of the screen are 4 icons which control the display of the risk tree. The 2 icons near the top right border, control the number of levels above the current node that are displayed. Icon 871 will increase by '1' the number of levels above the current node that are to be displayed, while icon 872 will decrease by '1' the number of levels above the current node that are to be displayed. The current value for the number of levels above the current icon that is to be displayed is itself displayed 873 and cannot have a value less than '0'. The 2 icons near the bottom right border, control the number of levels below the current node that are displayed. Icon 876 will increase by 1 the number of levels below the current node that are displayed, while icon 877 will decrease by 1 the number of levels below the current node that are to be displayed. The current value for the number of level below the current icon that is to be displayed is itself displayed 878 and cannot have a value less than '1'.

The user interacts with the risk assessment displayed on the screen using a mouse, touchscreen or other pointing device. If the user points and clicks the mouse at the 'Restart' icon 861, then the display will be redrawn to the original display with the start node as the current node. If the user points and clicks the mouse at the 'Switch Display Context' icon 862 then the display will switch to 'Text' mode if it is in 'Tree' mode and 'Tree' mode if it is in 'Text' mode. An example of a risk assessment screen in 'Text' mode is given in FIG. 11.

If the user points the mouse on any of the boxes 811, 812, or 813 then the text associated with the box is displayed as a popup tooltip text. For instance, if the user points the mouse at box 811, then the popup tooltip text will display the full text of the question in box 811. This is necessary in cases where because of the number of risk assessment questions that are displayed the full text of the question cannot be displayed in the text box. An example of this is given in FIG. 9. If the user points at the small response boxes 831, 832 then the associated response is displayed in a popup tooltip text, and is also necessary for large trees where the response cannot be fully displayed on the screen. Tooltip text 841 is an example of response tooltip text when the user points the mouse cursor in response box 831.

If the user points and clicks the mouse at question 812 or at response box 831 then the user is selecting 'No' 835 as the response to the current question 811. This action will cause the risktree-client to redraw the risk assessment display, identifying question 812 as the current question and using a heavier width line to draw the line between questions 811 to 812 to indicate the question/response path clearly to the user.

If the user points and clicks the mouse at icon 871 then the number of levels to be displayed above the current question will be increased by '1', the new value displayed 873, and the risk display redrawn to reflect the new value. If the user points and clicks the mouse at icon 872, and the number of levels to be displayed above the current question is greater than '0', then the number of levels to be displayed above the current question will be decreased by '1', and the new value displayed 873, and the risk display redrawn to reflect the new value. Similar actions will ensue if one points and clicks at the icons controlling the number of levels that will be displayed below the current node. If the user points and clicks the mouse at icon 878 then the number of levels to be displayed below the current question will be increased by '1', the new value displayed 878, and the risk display redrawn to reflect the new value. If the user points and clicks the mouse at icon 877, and the number of levels to be displayed below the current question is greater than '1', then the number of levels to be displayed below the current question will be decreased by '1', and the new value displayed 878, and the risk display redrawn to reflect the new value.

The set of responses from which a user may choose, are limited to those responses to the current question. If the user points and clicks at any other response, a message box 'Invalid selection' is displayed. The user may point and click at any prior question in the tree to deselect their prior response. The set of question boxes that the user may return to is limited to those questions that they have already responded to and are clearly indicated by their connection with a heavier weight line. If the user points and clicks at any other question box in the display then a message box 'Invalid selection' is displayed.

Not shown on FIG. 8 is the popup risk assessment information box. If the user of the risk assessment points and clicks the mouse at any place on the display, and clicks with the right mouse button, then an risk assessment information box is displayed. The popup risk assessment information box displays information about the risk assessment and includes the 'Definition of the risk to be assessed' 511, 'Source of the risk decision rule' 512, 'Network location of risk definition file' 513, 'E-mail address' 518, and the date range 516, 517 that the risk assessment is valid.

Figure 9:
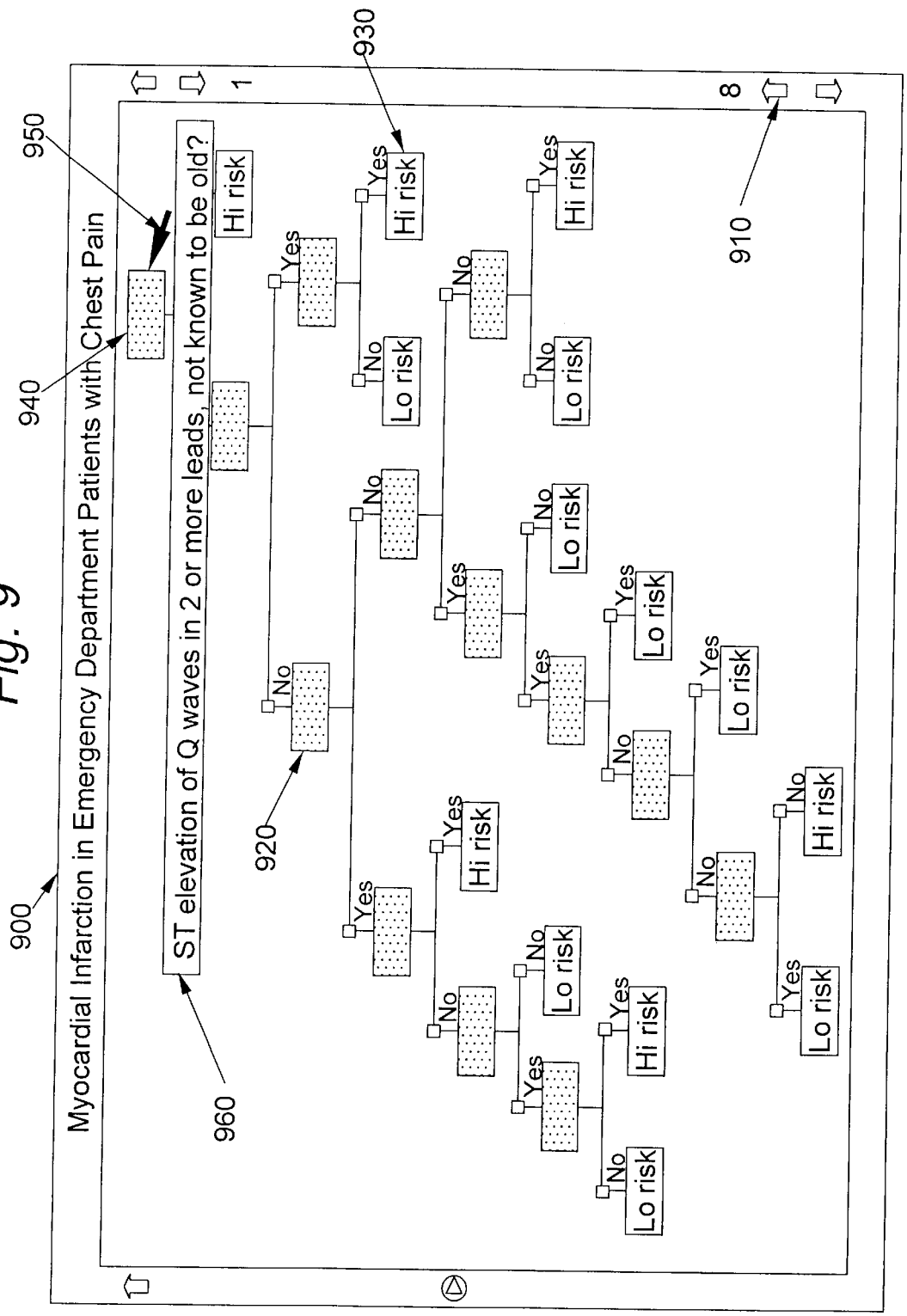
FIG. 9 is an example of a risk assessment screen showing a customized view of the risk assessment tree display.

FIG. 9 shows the main display 900 of the risktree-client at the beginning of the assessment for the risk of myocardial infarction in emergency department patients with chest pain. The risk assessment is still at the first questions as in FIG. 8, but the number of levels to be displayed below the current question has been set to 8, through the use of the icon 910, resulting in a display of the entire risk assessment tree. The user interaction with the display operates the same as described for FIG. 8. The question boxes 940 is now to small to display the text of the question, so the user may see the full text by pointing the mouse 950 at the question box and the popup tooltip text 960 is displayed with the text of the full question.

Figure 10:
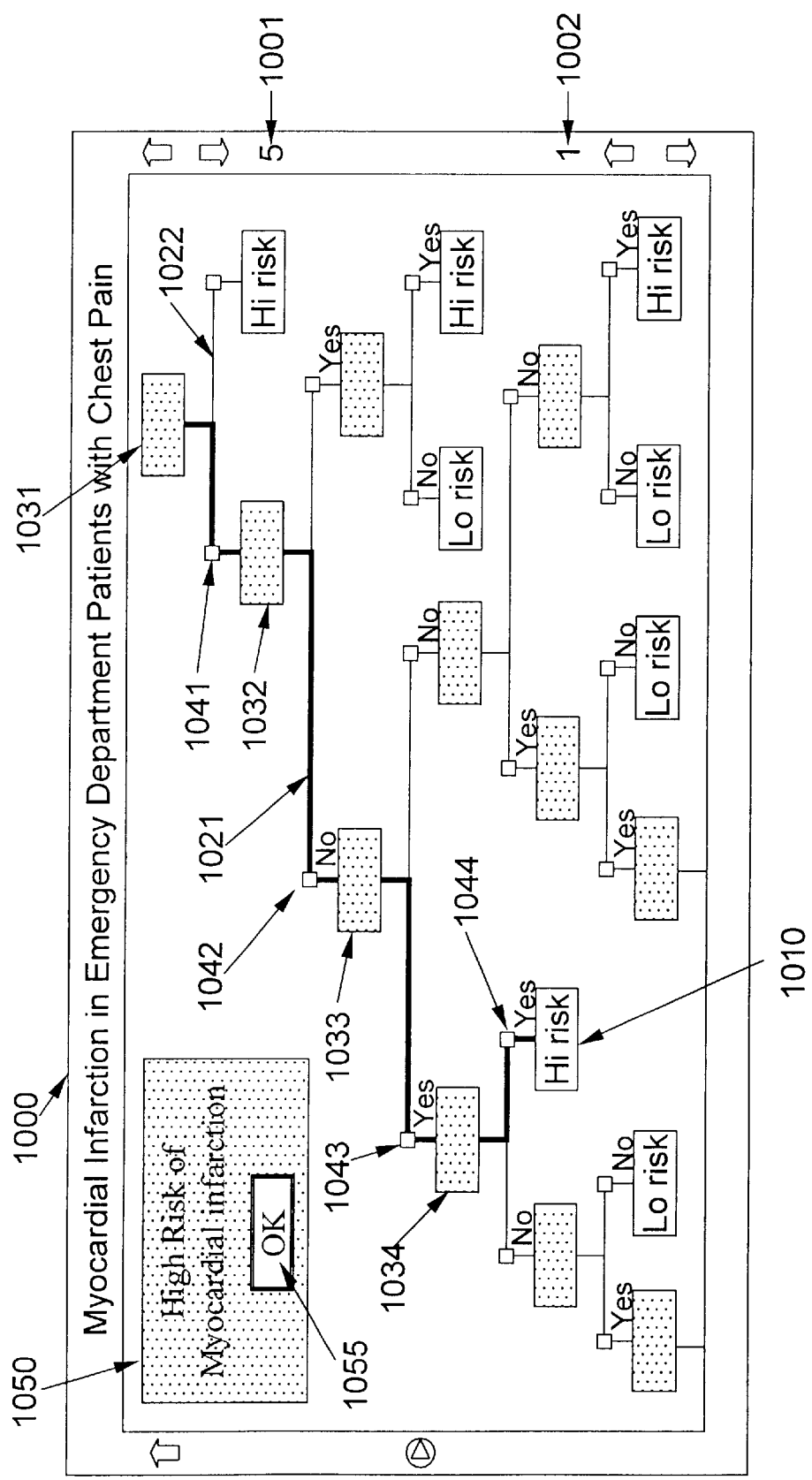
FIG. 10 is an example of a risk assessment screen showing the display in tree display format at the conclusion of a risk assessment.

FIG. 10 shows the main display 1000 of the risktree-client after the user has responded to four questions in the risk assessment. The 'Tree' display mode still has the same functionality described in FIG. 8. This display has the number of levels displayed above the current question set to '5' 1001 and the number of levels displayed below the current question set to '1' 1002. The current node 1010 has a highlighted border to make it easier to distinguish. Note that the lines 1021 are darker than the lines 1022. The heavier weight lines show the user clearly the path that they have taken through the tree to get to the current stage of the interactive risk assessment.

In this example the user has responded to the first question 1031 with a 'No' 1041; responded to question 1032 with a 'No' 1042; responded to question 1033 with a 'Yes' 1043, and responded to question 1034 with a 'Yes' 1044. This takes the user to the end of the risk assessment at terminal node 1010, and the risk assessment is displayed in a popup risk box 1050 which displays the result of the risk assessment 'High risk of myocardial infarction' on the display monitor. When the user responds to the 'OK' button 1055, the risk assessment is redisplayed at the beginning of the risk assessment as seen in FIG. 8.

Figure 11:
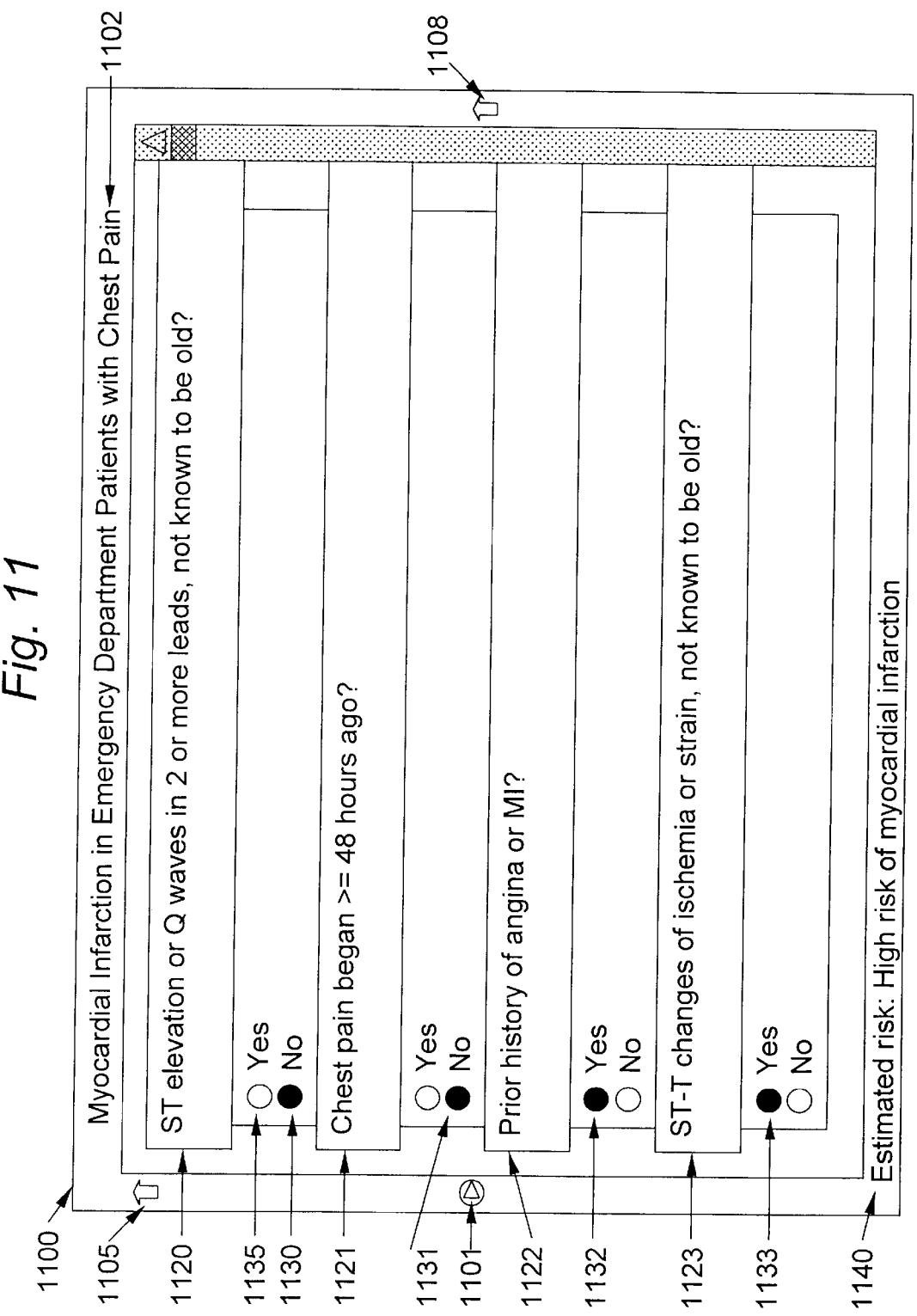
FIG. 11 is an example of a risk assessment screen showing the display in text display format at the end of a risk assessment.

FIG. 11 shows the main display 1100 of the risktree-client if the user had chosen to perform the risk assessment in 'Text' mode. The display mode 'Text' is chosen when the main display is in 'Tree' display mode by pointing and clicking at the 'Change Display Mode' icon 867 of FIG. 8. The display mode 'Tree' is chosen when the main display is in 'Text' display mode by pointing and clicking at the 'Change Display Mode' icon 1101 of FIG. 11. In each case, selecting the 'Change Display Mode' icon causes the display mode to be toggled to the other setting, and the risk assessment display to be redrawn in the new setting. The risk assessment display of FIG. 11 corresponds to the same stage of the risk assessment as is displayed in FIG. 10; i.e. both risk assessments have selected the same responses to all questions.

A title box 1102 at the top of the computer monitor of the risktree-client identifies the type of risk that is being assessed; 'Myocardial Infarction in Emergency Department Patients with Chest Pain' as given in record 1 of the risk definition file. Along the left edge of the screen are two icons. The 'Restart' icon 1105 will be used to restart the risk evaluation over at the start node, and the 'Switch Display Context' icon 1102 is used to switch the risk evaluation to 'Tree' display mode, but maintaining the same position in the risk assessment.

In this example the user has responded to the first question 1120, 'ST elevation or Q waves in 2 or more leads, not known to be old' with a 'No' 1130; responded to question 1121 'Chest pain began more than 48 hours ago?' with a 'No' 1131; responded to question 1122 'Prior history of angina or MI?' with a 'Yes' 1132, and responded to question 1123 'ST-T changes of ischemia or strain, not known to be old?' with a 'Yes' 1133. This takes the user to the end of the risk assessment, and the risk assessment is displayed in the risk assessment text box 1140 at the bottom of the screen which displays the result of the risk assessment 'High risk of myocardial infarction' on the display monitor.

The program displays the user's response to a question by shading the circle just to the left of the response. The response to question 1120 'No' 1130 was shaded when the user selected that response, while the 'Yes' response 1135 to question 1120 is left unshaded.

The 'Text' display mode does not display the tree structure. Rather, it starts off by displaying only the first question and the set of valid response. The valid responses are drawn without any shading indicating that it is the current question and that no choice has been made. The user may point and click at either of the valid responses to select that response. In FIG. 11 the valid responses to the first question 1120 'ST elevation or Q waves in 2 or more leads, not known to be old"' are 'Yes' 1135, and 'No' 1130. Selecting a response has the effect of redrawing the risk assessment screen with the selected response shaded and either adding the next question and its set of valid responses to the display, or if the risk assessment has reached a terminal node, displaying the risk assessment in the risk assessment text box 1140.

Along the right edge of the screen is a single 'Prior Question' icon 1108. Pointing and clicking the mouse at this icon deselects the last response in the risk assessment and redraws the display. In the case of FIG. 11, the answer 'Yes' 1133 to the question 'ST-T changes of ischemia or strain, not known to be old?' will be deselected and the display screen redrawn without the response shading. The user may also deselect prior responses, and return to any prior question by pointing and clicking at any displayed question 1120, 1121, 1122, or 1123, in which case the risk assessment screen will be redisplayed showing the selected question, all prior questions and their responses, and with none of the responses to the selected question shaded.

E. System state diagram

Figure 12:
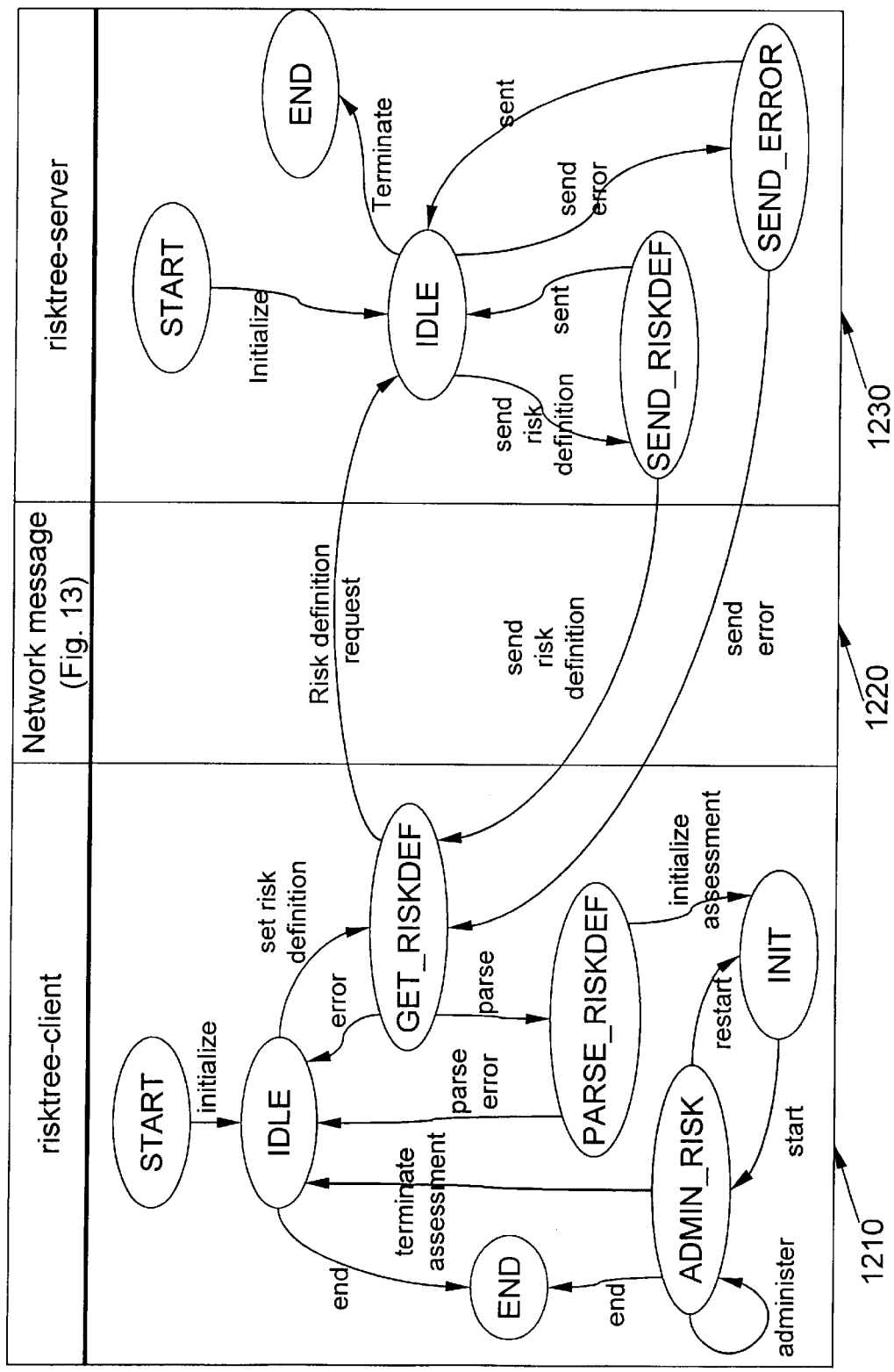
FIG. 12 is a state diagram describing the operation of the client and server programs.

FIG. 12 is a state diagram 1200 showing the state machines describing the (1) operation of each of the risktree-client, (2) risktree-server and ,(3) messaging interface between the components of the system. State tables that provide details of the operation of the risktree-client, and risktree-server are presented in FIG. 14, and 15, respectively, and details of the message protocols in FIG. 13.

FIG. 12 has 3 separate regions. The region labeled risktree-client 1210 shows the state machine for the operation of the risktree-client; the region labeled risktree-server 1229 shows the state machine for the operation of the risktree-server; and the region labeled 'NetworkMessage FIG. 13' 1230 is the network message interface between the risktree-client and the risktree-server and is described in detail in FIG. 13. The state machine diagrams show the different of the program, and the actions which cause them to change state. Arrows pointing to-and-from the Network-Message regions show the interprocess communication over the network between the different components of the system, and in particular show which states may send/receive network messages.

The risktree-client state machine 1210 has 7 states. In the state 'START' the program is started and after initialization of program variables transfers to the state 'IDLE'. In state 'IDLE' the risktree client waits for a request from the user. If the requested action is to end the risk assessment, then the program transitions to the 'END' state and halts execution. If the requested action is to get a risk definition then the program checks for the validity of the URL that specifies the risk definition and if it is valid, transitions to the state 'GET_RISDKDEF' to start the processing to retrieve and parse the risk definition. If it is an invalid URL then display the message 'Illegal name' and wait in the state 'IDLE' for another request.

The risk definition file is specified by a URL which gives the location, either local or on the network for the risk definition. State 'GET_RISKDEF' first checks to see if there a copy of the risk assessment on the local machine. If there is copy of the risk definition file on the local machine, then the file is retrieved and the program transitions to the state 'PARSE_RISKDEF' to continue processing. If there is not a copy of the risk definition file on the local machine then (1) format a request for the risk assessment (2) connect with the risktreeserver (3) request the risk definition (4) wait and retrieve the response from the risktree-server, and (5) disconnect with the server. If the response is a risk definition then transition to the state 'PARSE_RISKDEF', but if the response is an error message then display the error message and transition to the 'IDLE' state. All network communication for the risktree-client is performed in the state 'GET_RISKDEF'.

State 'PARSE_RISKDEF' parses the risk definition file, saves all the fields 511–518 in the risk definition file in variables in the program, as well as the node-descriptor variables for each node in the risk definition node tree. The maximum depth of the risk assessment is also set and saved. If there is an error during the parsing then display the error message 'Error in Parse' and transition to the state 'IDLE', else transition to the state 'INIT' to continue processing.

In the state 'INIT' several variables are initialized that will be required during each risk assessment session. This includes setting the display mode to 'Tree' and setting the current question to the first question in the risk assessment. After this initialization is performed the program transition to state 'ADMIN_RISK' to administer the risk assessment to the user.

IN the state 'ADMIN_RISK' there are 3 types of actions that cause the program to transfer to another state. The user may request that the risk assessment be restarted in which case the program transfers to the state 'INIT' to reinitialize the risk assessment to its initial state. The user may choose to end the risktree-client, in which case the program transitions to the state 'END' and the program terminates execution, or the user may request that a new risk assessment be administered in which case the program transitions to the state 'IDLE' so the program can acquire the risk definition file for the new risk assessment. All other actions in the 'ADMIN_RISK' state result in the program remaining in the state 'ADMIN-RISK', and relate to the interactions between the user and the risktree-client as the user responds to questions and chooses different customization options to assist them in the risk assessment. The details of these actions will be described in FIG. 15.

The risktree-server state machine 1210 has 5 states. In the state 'START' the program is started and after initialization of program variables transfers to the state 'IDLE'. In state 'IDLE' the risktree-server waits for a request for service. The request may be an operator request to terminate the risktree-server in which case the program transitions to the state 'END' and terminates execution, or the request may be a network request message. If the request is a network request then a connection is established with the requesting program and the request message is parsed. If the request if for an available risk definition then the program transitions to the state 'SEND_RISKDEF' to retrieve and send the file, and then terminates the connection and transitions back to the state 'IDLE' to await another request. Any other request will cause the risktreeserver to transition to the state 'SEND_ERROR' to send an error message, and then terminate the connection and transition back to the state 'IDLE to await another request.

There are three types of network messages 1230 that are used to communicate between the client and server portions of the system. All communication on the client side is performed in the state 'GET_RISKDEF' which sends a request for a file and receives the response. The communication on the server side is performed in the 'IDLE' state that receives requests, and the 'SEND_RISKDEF' and 'SEND_ERROR' state the process and fulfill the request. The network messages are described in further detail in FIG. 13.

F. Connection protocol

The preferred embodiment uses an industry standard ethernet and an industry standard TCP/IP network protocol for its computer network. A conversation between the risktree-client and the risktree-server is implemented by establishing a connection between the computers over the computer network. To minimize computer resources to maintain the connection between the risktree-server and the risktree-client, this invention uses a non-persistent network connection; i.e. a network connection is established between the interview-client and the interview-server only for the length of time necessary to perform a specific transaction. In the preferred embodiment the connection is implemented using the industry standard hypertext transport protocol (http). In other embodiments the non-persistent connection may be implemented using another industry standard protocol, or a special protocol may be implemented specifically to address the operation of the risk assessment. If either the risktree-client or the risktree-server program terminates their connection with the other program either by design or another reason, such as a network outage, the other program also terminates its connection state.

Figure 13:
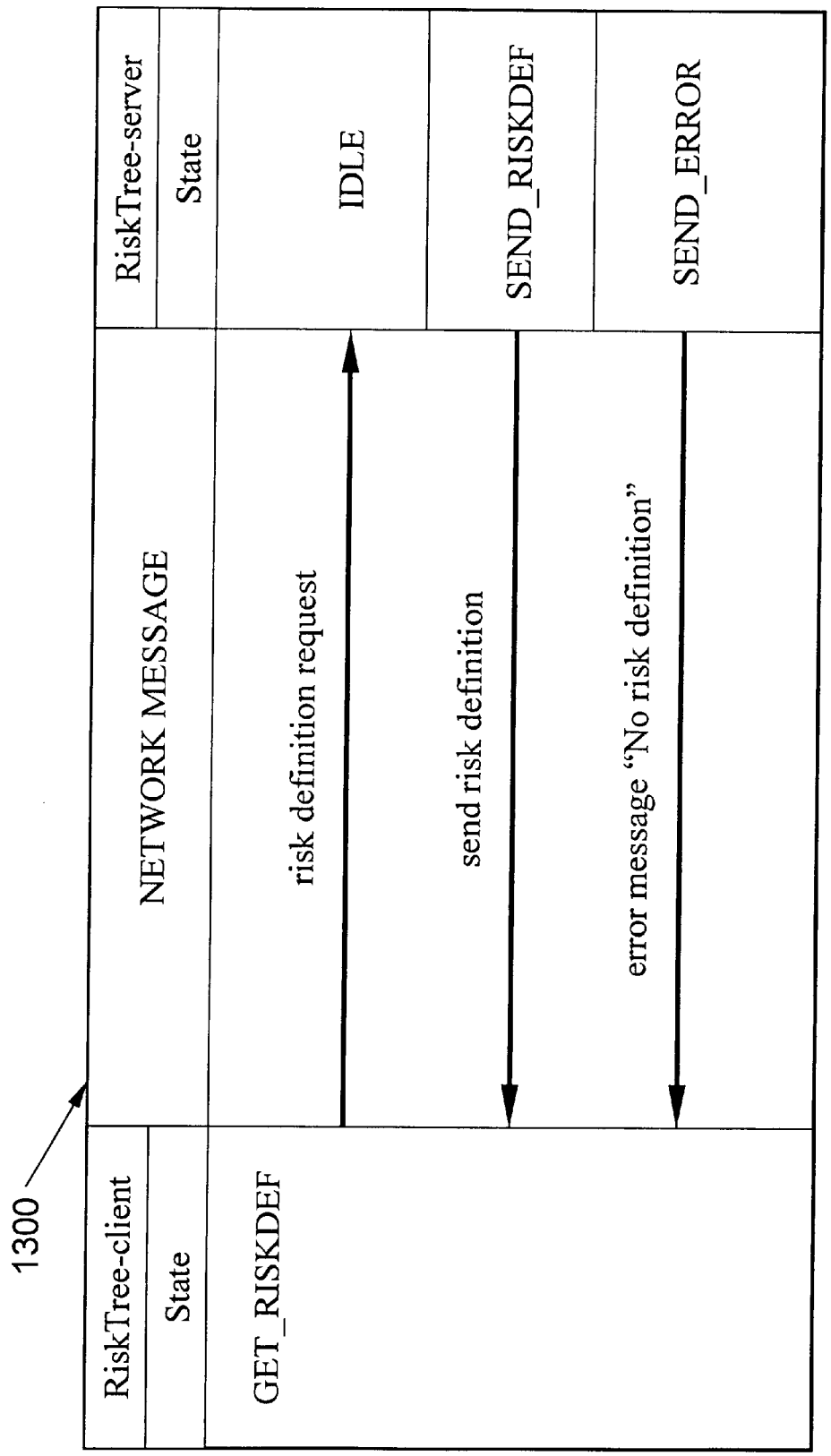
FIG. 13 displays the client/server program message protocols.

FIG. 13 is a diagram 1300 of the network message protocols for communications between the risktree-client and the risktree-server. It shows the risktree-client states on the left side of the figure and the risktree-server states on the right hand side of the figure. The messages that are sent from each state of the risktree-client and their response from the risktree-server are indicated on the diagram.

From state 'GET_RISKDEF' a request may be made to the risktree-server for a specific risk definition that the risktree-server maintains. After the request is sent the risktree-client waits in the state 'GET_RISKDEF' to receive the response from the risktree-server.

The risktree-server responds by establishing the connection, retrieving and parsing the message. If the message is valid and the risk definition is available then the risktree-server transitions to state 'SEND_RISKDEF' and sends the risk definition file to the risktree-client.

If the message is not valid, or the message is valid but the risk definition is not available, for whatever reason, then the risktree-server transitions to the state 'SEND_ERROR' and sends the error message to the risktree-client. After the risktree-client receives the risk definition or an error message from the risktree-server, the risktree-client terminates the connection with the risktree-server.

G. Risk Assessment Server Program

Figure 14:
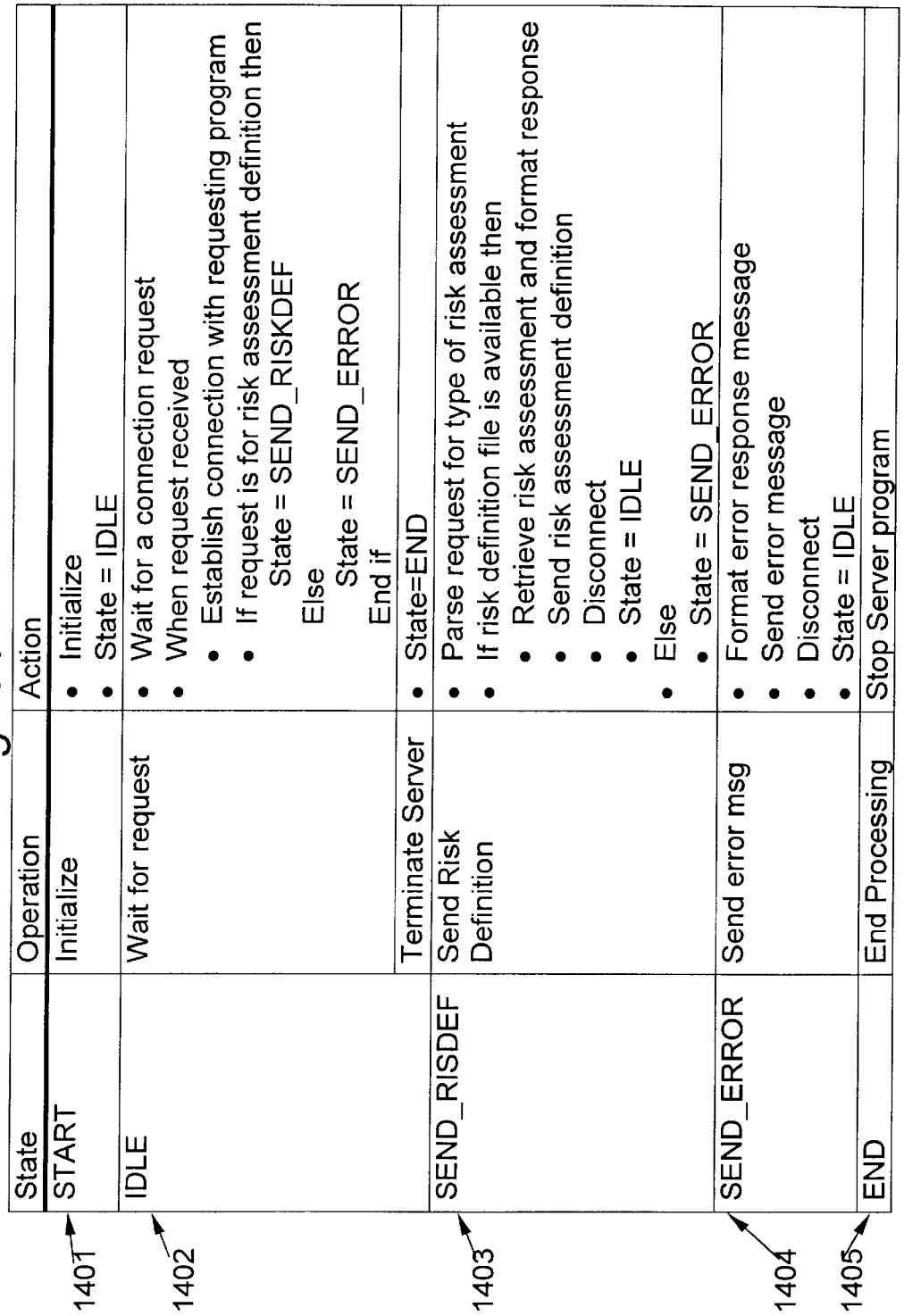
FIG. 14 is a state table describing the operation of the server program.

FIG. 14 is a diagram 1400 with a state table describing the operation of the risktree-server program. Upon initialization of the risktree-server it enter the START state 1401, performs initialization and transitions to the IDLE state 1402.

In the IDLE state 1402, the server waits for a request for a connection from a risktree-client. When a request for a connection is received the risktree-client establishes the connection with the risktree-client. If the request is for a risk assessment definition, then the program transitions to the state SEND_RISKDEF 1403 to fulfill the request. All other request messages are invalid and the program transitions to the state SEND_ERROR 1404 to send an error message.

Termination of the risktree-server occurs in response to a system or operator request to terminate the execution of the risktree-server program. During the IDLE state 1402, the risktree-server can receive a system or operator request to terminate the risktree-server processing, in which case the program transitions to the state END 1405, performs shutdown processing, and terminates the execution of the risktree-server program.

State SEND_RISKDEF 1403 is used to process a request for a risk assessment defintion. When the program enters this state, a connection is already established with the risktree-client. The irisktree-server program parses the name of the risk assessment definition that has been requested, and checks for the availabity of the risk assessment definition. If the risk assessment definition is available then it retrieves the file, and transmits this file to the risktree-client program using the industry standard hypertext transport protocol. At the successful completion of the transmission, the connection is terminated by the risktree-server, and the program transitions back to the state IDLE 1402 to await the next service request. If the risk definition is not available, then the risktree-server transitions to the state 'SEND_ERROR' 1404.

State 'SEND_ERROR' 1404 is used to indicate that no risk assessment definition can be provided by the risktree-server. The risktree-server formats a one line error response message "ERROR-NO RISK DEFINITION" and transmits the response to the risktree-client program using the industry standard hypertext transport protocol. At the successful completion of the transmission, the connection is terminated by the risktree-server, and the program transitions back to the state IDLE 1402, to await the next service request.

State 'END' 1405 stops the execution of the risktree-server program.

H. Risk assessment client program

Figures 15, 15A:
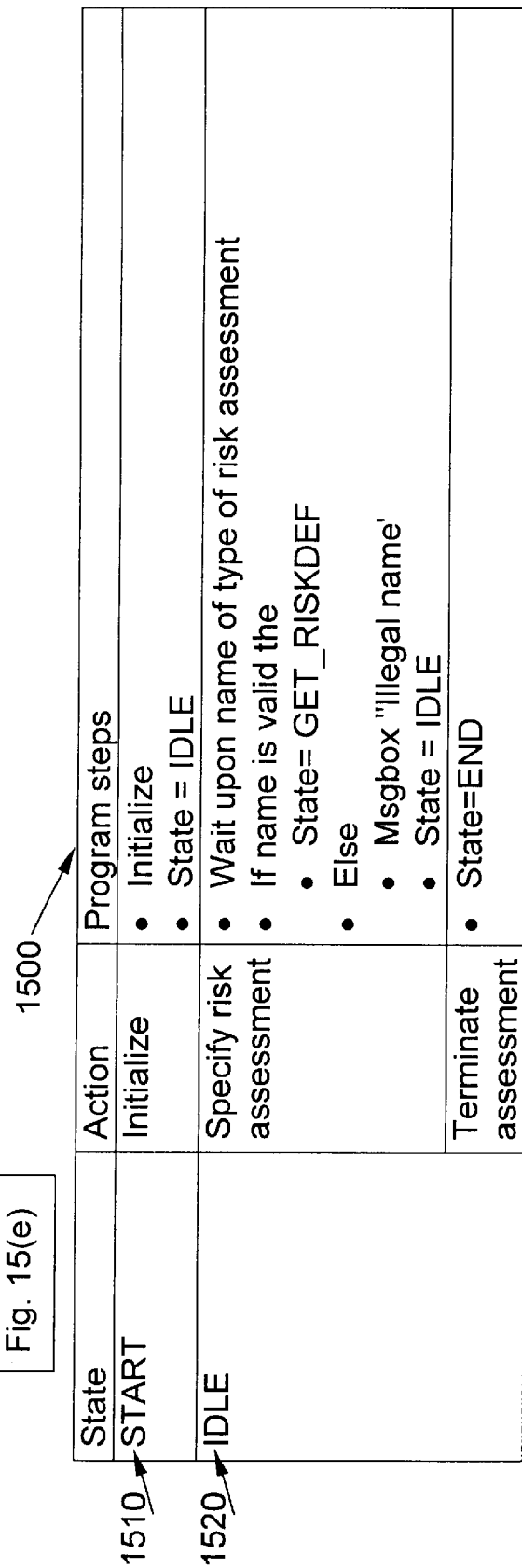
FIG. 15 is a state table describing the operation of the client program.
Figure 15C:
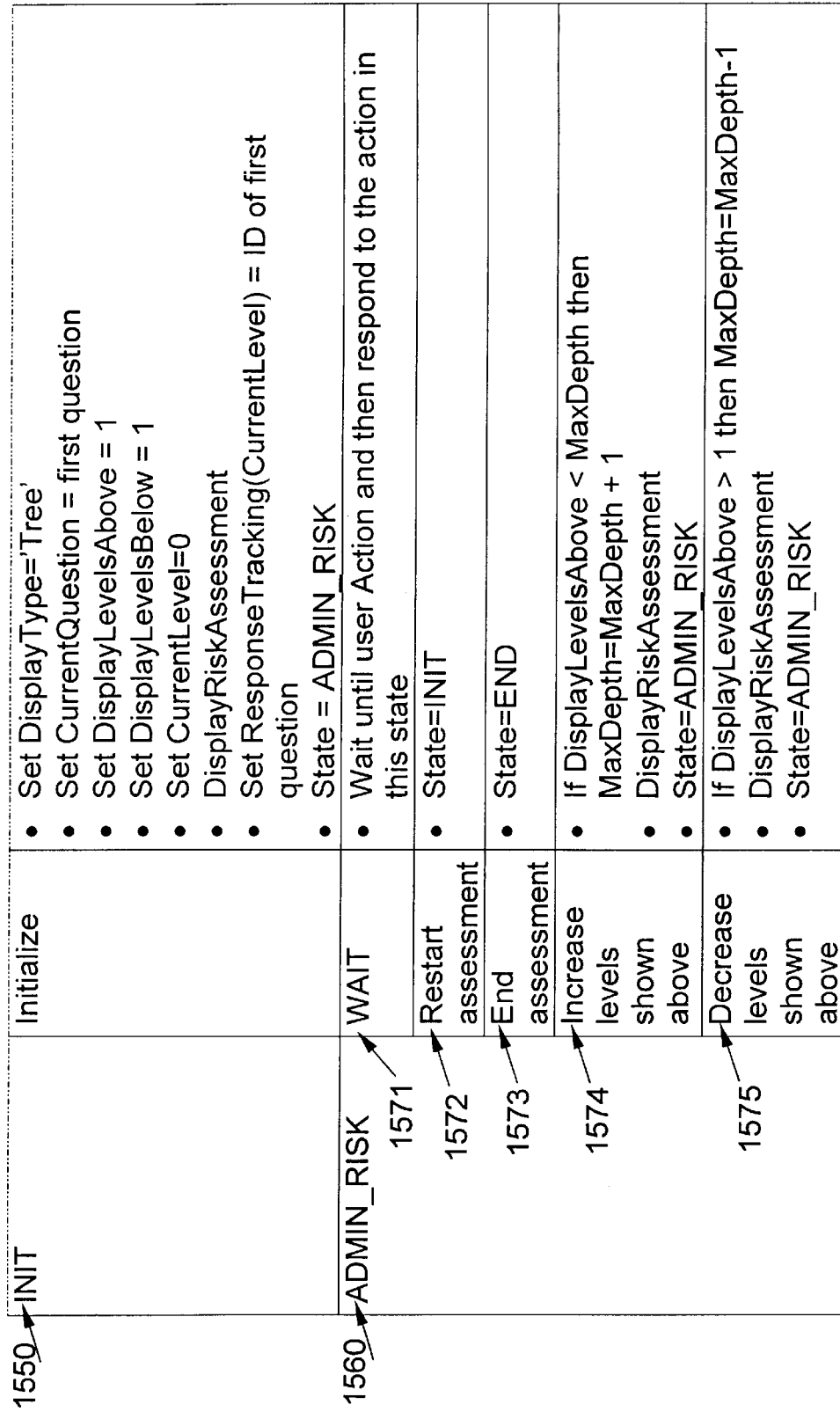
Figure 15E:
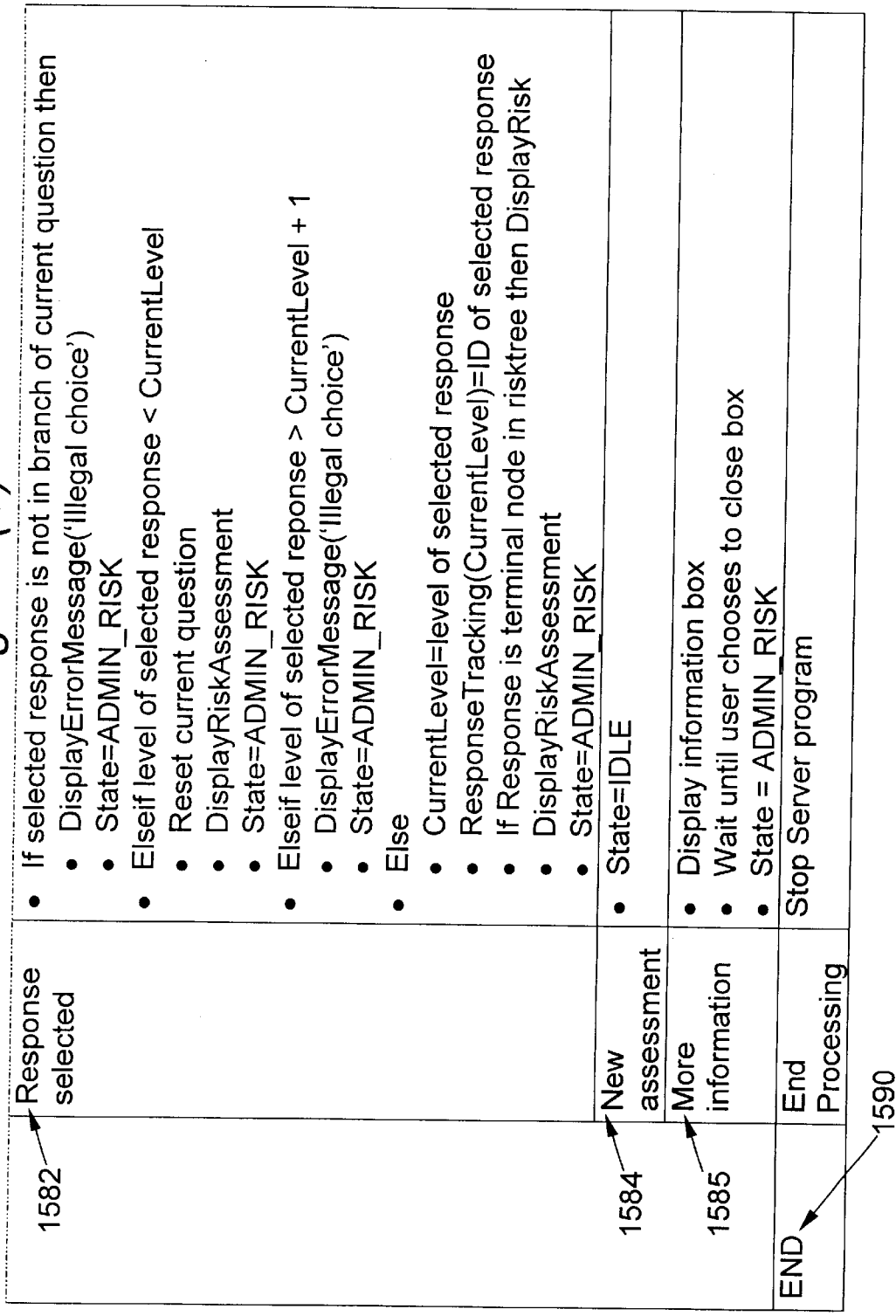

FIG. 15 is a diagram 1500 with a state table describing the operation of the risktree-server program. Upon initialization of the risktree-server it enter the START state 1510, performs initialization and transitions to the IDLE state 1520.

In the 'IDLE' state 1520, the risktree-client program waits for a user requested action. The user may either request that the program be terminated in which case the program transitions to state 'END' for termination processing or the user may request that a risk assessment be performed by specifying the URL of the risk definition that is to be administered. The program then validates the URL of the risk definition. If the URL is a valid resource, then the program transitions to the state 'GET_RISKDEF' to continue processing. If the URL is invalid then the program displays the error message 'Invalid name' and continues in the 'IDLE' state.

In the 'GET_RISKDEF' state 1530, the risktree-client program first parses the name of the risk definition file from the URL and checks to see if there is a copy of the risk definition file on the client machine. If there is then retrieve it and transition to the state 'PARSE_RISKDEF' 1540. If the risk definition is not resident on the client machine, then (1) format the network request for the risk definition file (2) connect with the risktree-server (3) request the risk assessment from the risktree-server, and (4) wait for a response. When the response is received from the risktree-server check to see if it is an i error message, and if it is then display the error 'No risk definition' to the user and transtion to the state 'IDLE'. If the response is the risk definition file then store it, and transition to the state 'PARSE_RISKDEF' 1550.

In the state 'PARSE_RISKDEF' 1550 parse the risk definition. If during parsing an error is encountered, then display the error message 'Risk definition error' and transition to the state 'IDLE' 1520. If the parse is completed without error, then the values from the parsing will have been saved in risktree-client program memory, and will include all the information in the risk definition structure of FIG. 5, which is saved in the internal data structure described in FIG. 7. Then the program will transition to the 'INIT' state 1550, to initialize the risk assessment interactive program.

In the state 'INIT' 1550, the risktree-client is initialized to the first question in the risk assessment, the risk assessment displayed to the user, and the interface enabled to accept user input from the mouse pointing device. The display mode is set to 'Tree' indicating that the initial display mode is 'Tree' mode, and the currentQuestion is set to the 'NodeID' 710 of the first node in the risk assessment decision tree. The value for the number of levels to be shown above and below the current question are both set to '1', and then the risk assessment is displayed to the user. Then transition to the state 'ADMIN_RISK' to begin the interactive self administered risk assessment.

State 'ADMIN_RISK' 1560 administers the risk assessment to the user. The program waits until the user interacts with the interactive risk assessment by pointing and clicking with the imouse pointing device 230, performs the requested action, and continues processing. The user can choose to restart the risk assessment by using the mouse to point and click at the 'Restart' icon (861 in 'Tree' mode and 1105 in 'Text' mode). This will cause the program to immediately terminate the current risk assessment and transfer to the state 'INIT' 1550 to reinitialize and restart the risk assessment.

The user can choose to terminate the risk assessment program in either 'Tree' or 'Text' display mode, by using the right mouse button to bring up a context sensitive popup menu and choosing the 'EXIT' option. This will cause the program to immediately terminate the current risk assessment and transfer to the state 'END' 1590 to terminate the execution of the risktree-client program.

In 'Tree' display mode, the user controls the number of levels above and below the current question that are displayed. The user can choose to 'Increase levels shown above' 1574, by pointing and clicking the mouse at the 'Increase levels above' icon 871, which causes the program to check if the current value is less than the maximum number of levels and if it is then increase it by '1', redraw the risk assessment screen to reflect the new value, and continue processing in the state 'ADMIN_RISK'. The user can choose to 'Decrease levels shown above' 1575, by pointing and clicking the mouse at the 'Decrease levels above' icon 872, which causes the program to check if the current value is greater than '1', and if it is then decrease the parameter by '1', redraw the risk assessment screen to reflect the new value, and continue processing in the state 'ADMIN_RISK'. The user can choose to 'Increase levels shown below' 1576, by pointing and clicking the mouse at the 'Increase levels below' icon 877, which causes the program to check if the current value is less than the maximum number of levels and if it is then increase it by '1', redraw the risk assessment screen to reflect the new value, and continue processing in the state 'ADMIN_RISK'. The user can choose to 'Decrease levels shown below' 1577, by pointing and clicking the mouse at the 'Decrease levels below' icon 876, which causes the program to check if the current value is greater than '1', and if it is then decrease the parameter by '1', redraw the risk assessment screen to reflect the new value, and continue processing in the state 'ADMIN_RISK'.

The user can choose to 'Change display mode' 1578, by pointing and clicking at the 'Toggle display' icon ('Tree' display mode 867, 'Text' display mode 1101). If the display is in 'Tree' mode then the display is redrawn in 'Text' mode and the processing continues in the state 'ADMIN_RISK'. If the display is in 'Text' mode then the display is redrawn in 'Tree' mode and the processing continues in the state 'ADMIN_RISK'. In 'Text' display mode the user can choose the action 'Prior question' 1579, by pointing and clicking the mouse pointer on the prior question icon 1108 causing the risk assessment display to be redrawn in 'Text' display mode, with the prior question as designated as the current question, and then continuing the processing in the state 'ADMIN_RISK'.

In 'Tree' display mode, the action 'MouseOver Question' icon 1580 is initiated whenever the user moves the position of the mouse 950 over a 'Question' icon 940, causing the full text of the question to be displayed in a popup text box, and which disappears when the mouse pointer is moved out of the text box. Also in 'Tree' display mode, the action 'MouseOver Response' icon 1581 is initiated whenever the user moves the position of the mouse 840 over a 'Response' icon 831, causing the full text of the response to be displayed in a popup text box, and which disappears when the mouse pointer is moved. In either case the processing continues in the state 'ADMIN_RISK'.

The user can choose to answer a risk assessment question 1582 by pointing and clicking the mouse (1) on a response icon, or (2) at a question icon, which causes the selection of the associated response icon. If the chosen answer is not in a branch of the current question then display the error message 'Illegal choice', and continue processing in the state 'ADMIN_RISK'. If the chosen answer is in the branch of the tree of the current question and the level of the selected response is less than the level of the current question, then reset the current question, redisplay the risk assessment, and continue processing in the state 'ADMIN_RISK'. If the chosen answer is in the branch of the tree of the current question and the level of the selected response is more than '1' greater than the level of the current question, indicating the user has skipped a question, then display the error message 'Illegal choice', and continue processing in the state 'ADMIN_RISK'. In all other cases, set the current question to the question associated with the selected response. If the current question is a terminal node of the risk assessment then display the estimated risk assessment and continue processing by reinitializing the risk assessment in the state 'IDLE', but if it is not a terminal node the, display the risk assessment in the current display mode and continue processing in the state 'ADMIN_RISK'.

The user can choose to run a 'New assessment' 1584, in either 'Tree' or 'Text' display mode, by using the right mouse button to bring up a context sensitive popup menu and choosing the 'NEW' option. This will cause the program to immediately terminate the current risk assessment and transfer to the state 'IDLE' 1520 so the user may specify another type of risk assessment to be administered by the risktree-client program. Another action, in either 'Tree' or 'Text display mode, that the user can initiate is to view the additional ' Information '1585' that is provided in the risk definition file about the risk assessment. This includes the source of the risk decision rule 512, network location of the risk definition file 513, date range during which the risk assessment is valid (516, 517), and an E-mail contact address 518. This information is accessed by the user by using the right mouse button to bring up a context sensitive popup menu and choosing the 'HELP' option. This will cause the program to display this information on the screen with a screen button with the label 'Okay' that when depressed will remove the information screen from the display monitor, and continue processing in the state 'ADMIN_RISK'.

In the 'END' state 1590, the risktree-client terminates execution of the risktree-client program.

3. Other Embodiments

Other embodiments of the inventions use the same principles to implement a system to perform a self administered interactive risk assessment. In the preferred embodiment there are customization options to control the amount of information that is displayed and the manner in which the risk assessment is presented. This can be further enhanced with other customization options that further assist the user to understand and operate the risk assessment, and other display formats. Also other kinds of information may be made available to give further explanations of the questions and responses. What is important is that these z5 additional customization options aid the user in understanding how to operate the risk assessment.

In other embodiments there may be other means to calculate the risk. In the current embodiment, a risk value is associated with each terminal node. Other means to calculate the risk might include summing values based on the response to each question, and translating that value into a risk when a terminal node is reached.

In other embodiments the risk assessment decision procedure may follow formats other than that of an inverted tree. Decision structures in which the sequence of questions is entirely predetermined and not dependent upon the response to the prior question, or structures in which responses to different questions can lead to the same question may be accommodated by the system.

In still other embodiments the structure of the risk definition file may be extended to include other decision algorithms that may not be able to be coded by the current scheme.

In still other embodiments, the system may be used to assign group membership. The risk assessment process of answering questions until a terminal node is reached and a risk assigned is one of deciding that a person belongs in a group based on their responses to questions, and then giving a risk of occurance of an event associated with membership in that group. The system could be used equally well if the decision at a terminal node is to assign the person to a group without necessity of inferring a risk value.

Other embodiments will be apparent to those skilled in the art from consideration of the specification and practice of the invention disclosed herein. It is intended that the specification and examples be considered as exemplary only, with a true scope of the invention being indicated by the following claims.

What is claimed is:

1. A distributed computer system for performing a self administered interactive medical risk assessment, comprising:
   (a) a client program executing on a first computer;
   (b) a server program executing on a second computer;
   (c) a computer network using a non-persistent network protocol;
   (d) a risk assessment definition file that defines the risk assessment to be administered by the client program at the first computer to a user;
   (e) means for the user to select the risk assessment that is to be administered by said client program;
   (f) means for said client program to request and download the risk assessment definition file from the second computer over said computer network; and
   (g) client administer means for said client program to administer the selected risk assessment at the first computer, wherein said client administer means executes a program comprising the steps of:
      (i) visually displaying a portion of the risk assessment as a tree diagram;
      (ii) allowing the user to respond to a question from the selected risk assessment; and
      (iii) updating the risk assessment to reflect the most recent response by displaying an evaluated risk if the response was to a terminal question, otherwise redisplaying the risk assessment as in step (i);
   wherein a user assesses their own risk using complicated inverted tree type risk assessment algorithms.

2. The system as recited in claim 1 wherein said risk definition file includes:
   (a) a description of the risk that is being assessed;
   (b) the text of each question in the risk assessment;
   (c) identification of the first question in said risk assessment;
   (d) the text of the allowable responses associated with each question; and
   (e) the action to be taken in response to a question during the interactive risk assessment, wherein the action is either the specification of the next question to be displayed, or that the risk assessment is completed; wherein a data definition describing a complicated risk assessment can be updated and maintained; and wherein different risk assessments can be maintained on the second computer for display by said client program on the first computer.

3. The system as recited in claim 1, wherein said client administer means further executes a program comprising the steps of:
   (i) visually showing a portion of the tree-structure risk assessment that
      (1) includes the current question and its associated response(s), and for each of its said associated response(s), their associated next question or terminal state; and visually indicates the relationship between the current question and its associated response(s), and for each of its said associated response(s), visually indicates the relationship with their next question or terminal state;
      (2) for all prior displayed answered questions, visually indicates the path of questions, associated responses and next questions that lead to the current question in the risk assessment; and
      (3) visually indicates which question is the current question that is to be responded to by the user in the risk assessment;
   (ii) beginning the risk assessment by displaying a portion of the tree-structure as in (i) above, with the current question being the first question in the risk assessment;
   (iii) allowing the user to respond to the current question by responding to one of the responses associated with the current question, and resetting the current question to the question associated with the selected associated response; and
   (iv) updating the risk assessment to reflect the most recent response by displaying the evaluated risk or associated response if the most recent response was to a terminal question, or redisplaying the risk assessment as in (i) above if the most recent response was not to a terminal question.

4. The system as recited in claim 3, wherein said step of visually showing a portion of the tree-structure risk assessment further comprises the step of including some of the prior questions answered by the user and their associated response(s), and for each prior associated response(s), their associated next question or terminal state; and for each said included prior question, visually indicating the relationship between the prior question and its associated response(s), and for each of its said associated response(s), visually indicating the relationship with their next question or terminal state.

5. The system as recited in claim 3, wherein said step of visually showing a portion of the tree-structure risk assessment further comprises the step of including subsequent questions and their associated response(s), and for each subsequent associated response(s), their associated next question or terminal state; and for each included subsequent question, visually indicating the relationship between the subsequent questions and its associated response(s), and for each of its associated response(s), visually indicating the relationship with their next question or terminal state.

6. The system as recited in claim 1, wherein the self administered interactive risk assessment requires a response to every question, and is question order dependent.

7. The system as recited in claim 1, wherein the second computer is a server accessed by the first computer using hypertext transport protocol.

8. The system as recited in claim 7, wherein said risk assessment definition file is associated with a uniform resource locator (URL).

9. A method of performing a user administered interactive medical risk assessment, the method comprising:

(a) executing a client program on a first computer;

(b) executing a server program on a second computer;

(c) initiating a computer network connection between the first computer and second computer using a non-persistent network protocol;

(d) using a risk assessment definition file to define the risk assessment to be administered by the client program at the first computer to a user;

(e) allowing a user to select the risk assessment that is to be administered by the client program;

(f) requesting and downloading the risk assessment definition file from the second computer over the computer network; and (g) using the client program to administer the selected risk assessment, at the first computer (i) visually displaying a portion of the risk assessment as a tree diagram;

(ii) allowing the user to respond to a question from the selected risk assessment; and (iii) updating the risk assessment to reflect the most recent response by displaying an evaluated risk if the response was to a terminal question, otherwise redisplaying the risk assessment as in step (i);

wherein a user assesses a risk using complicated inverted tree type risk assessment algorithms.

10. The method as recited in claim 9, wherein said risk definition file includes:

(a) a description of the risk that is being assessed;

(b) the text of each question in the risk assessment;

(c) identification of the first question in said risk assessment;

(d) the text of the allowable responses associated with each question; and (e) the action to be taken in response to a question during the interactive risk assessment, wherein the action is either the specification of the next question to be displayed, or that the risk assessment is completed;

wherein a data definition describing a complicated risk assessment can be updated and maintained; and wherein different risk assessments can be maintained on the second computer for display by said client program on the first computer.

11. The method as recited in claim 9, further comprising the steps of (i) visually showing a portion of the tree-structure risk assessment that (1) includes the current question and its associated response(s), and for each of its said associated response(s), their associated next question or terminal state; and visually indicates the relationship between the current question and its associated response(s), and for each of its said associated response(s), visually indicates the relationship with their next question or terminal state;

(2) for all prior displayed answered questions, visually indicates the path of questions, associated responses and next questions that lead to the current question in the risk assessment; and (3) visually indicates which question is the current question that is to be responded to by the user in the risk assessment;

(ii) beginning the risk assessment by displaying a portion of the tree-structure as in (i) above, with the current question being the first question in the risk assessment;

(iii) allowing the user to respond to the current question by responding to one of the responses associated with the current question, and resetting the current question to the question associated with the selected associated response; and (iv) updating the risk assessment to reflect the most recent response by displaying the evaluated risk or associated response if the most recent response was to a terminal question, or redisplaying the risk assessment as in (i) above if the most recent response was not to a terminal question.

12. The method as recited in claim 11, wherein the selected risk assessment is used for emergency room department patients.

13. The method as recited in claim 9, wherein the selected risk assessment requires a response to every question in order.

14. The method as recited in claim 9, wherein said requesting step (f) includes specifying a uniform resource locator (URL) of the risk definition file.

* * * * *